United States Patent
Montclare et al.

(10) Patent No.: US 9,777,041 B2
(45) Date of Patent: Oct. 3, 2017

(54) PROTEIN NANOFIBERS FROM SELF-ASSEMBLING PENTAMERS

(71) Applicant: New York University, New York, NY (US)

(72) Inventors: Jin Kim Montclare, New York, NY (US); Jasmin Hume, New York, NY (US)

(73) Assignee: New York University, New York, NY (US)

( * ) Notice: Subject to any disclaimer, the term of this patent is extended or adjusted under 35 U.S.C. 154(b) by 122 days.

(21) Appl. No.: 14/481,533

(22) Filed: Sep. 9, 2014

(65) Prior Publication Data

US 2016/0017278 A1 Jan. 21, 2016

Related U.S. Application Data

(60) Provisional application No. 61/875,147, filed on Sep. 9, 2013.

(51) Int. Cl.
*C07K 14/78* (2006.01)
*C07K 14/00* (2006.01)

(52) U.S. Cl.
CPC ............ *C07K 14/001* (2013.01); *C07K 14/78* (2013.01)

(58) Field of Classification Search
CPC ........ A61K 38/16; A61K 38/39; C07K 14/00; C07K 14/78
See application file for complete search history.

(56) References Cited

U.S. PATENT DOCUMENTS

| | | | |
|---|---|---|---|
| 7,030,208 B2 | 4/2006 | Yalpani | |
| 9,453,060 B2 * | 9/2016 | Montclare | C07K 14/78 |
| 2002/0164810 A1 | 11/2002 | Dukor et al. | |
| 2003/0003135 A1 | 1/2003 | Leung et al. | |
| 2004/0115180 A1 | 6/2004 | Abdelouahed | |

OTHER PUBLICATIONS

Gunasekar et al. Effects of Divalent Metals on Nanoscopic Fiber Formation and Small Molecule Recognition of Helical Proteins. Advanced Functional Materials. 2012, vol. 22, pp. 2154-2159.*
Hume et al. Engineered Coiled-Coil Protein Microfibers. Biomacromolecules. Jun. 18, 2014, vol. 15, pp. 3503-3510.*
Haghpanah et al., Artificial Protein Block Copolymers Blocks Comprising Two Distinct Self-Assembling Domains, ChemBioChem, 10: 2733-35 (2009). Jan. 1, 2009
Kotze et al., Chitosans for enhanced delivery of therapeutic peptides across intestinal epithelia: in vitro evaluation in Caco-2 cell monolayers, International Journal of Pharmaceutics, 159: 243-53. Jan. 1, 1997.
Shih et al., The production of poly(y-glutamic acid) from microorganisms and its various applications, Bioresource Technology, 79(3): 207-25. Jan. 1, 2001.

(Continued)

*Primary Examiner* — Jeffrey E Russel
(74) *Attorney, Agent, or Firm* — Hodgson Russ LLP

(57) ABSTRACT

A protein nanofiber comprised of self-assembling pentamers, and a method for producing the protein nanofiber, in which the protein upon which the nanofiber is based is a specific form of COMP. The proteins self-assemble via electrostatic interactions to form fibers that extend longitudinally.

14 Claims, 33 Drawing Sheets
(15 of 33 Drawing Sheet(s) Filed in Color)

(56) References Cited

OTHER PUBLICATIONS

Nuhn et al., Secondary Structure Formation and LCST Behavior of Short Elastin-Like Peptiedes, Biomacromolecules 2008, pp. 2755-2763, vol. 9, No. 10, American Chemical Society. Jan. 1, 2008.
Trabbic-Carlson et al., Effect of protein fusion on the transition temperature of an environmentally responsive elastin-like polypeptide: a role for surface hydrophobicity, Protein Engineering, Design & Selection 2004, p. 57-66, vol. 17, No. 1. Jan. 1, 2004.
Cho et al., Engineered Protein Polymers, Polymer Preprints (American Chemical Society, Division of Polymer 47(2): 227-228 (Sep. 2006). Sep. 1, 2006.
Guo et al., All-trans retinol, vitamin D and other hydrophobic compounds bind in the axial pore of the five-stranded coiled-coil domain of cartilage oligomeric matrix protein, EMBO Journal 17(18): 5265-5272 (1998). Jan. 1, 1998.
Megeed et al., Genetrically Engineered silk-elastinlike protein polymers for controlled drug delivery, Advanced Drug Delivery Reviews 54: 1075-1091 (2002). Jan. 1, 2002.
Gunasekar et al., Biochemistry 2009, 48 (36), 8559-8567. Jan. 1, 2009.
Kajava et al., Proteins: Structure, Function and Genetics, 1996, 24, 218-226. Jan. 1, 1996.
Malashkevich et al., Science 1996, 274, (5288), 761-765. Jan. 1, 1996.

\* cited by examiner

Fig. 22a-q

PROTEIN NANOFIBERS FROM SELF-ASSEMBLING PENTAMERS

CROSS REFERENCE TO RELATED APPLICATIONS

This application claims priority to U.S. Provisional application No. 61/875,147, filed on Sep. 9, 2013, the disclosure of which is incorporated herein by reference.

STATEMENT REGARDING FEDERAL FUNDING

This invention was made with Government support under Grant Numbers DMR-0820341 and DGE-2 0741714 awarded by National Science Foundation, and Grant Number W911NF-11-1-0449 from the Army Research Office. The United States Government has certain rights in the invention.

FIELD OF THE DISCLOSURE

The present invention relates generally to the field of nanofibers and more particularly to protein biomaterials capable of self-assembly to form nanofibers.

BACKGROUND OF THE DISCLOSURE

Certain proteins and peptides that occur in nature exhibit the ability to self-assemble into materials that have unique properties including elasticity, tensile-strength, toughness, and resilience. For example, spider silk is one of the strongest known fibers in nature. Other examples include β-amyloids like those responsible for Alzheimer's disease as well as optically active self-assembling reflectins, and on the mesoscale like the bundled α-helical coiled-coil elastic protein of the Giant Clam, *Tridacna maxima*. While nature has created many elaborate proteins capable of complex self-assembly and ligand binding, fabricating materials with the same level of structural and molecular specificity on various length scales remains a challenge.

Polymers are currently being used to generate fibers for tissue engineering scaffolds. Nonwoven nanofibril particulates composed of non-degradable and degradable polymers for tissue engineering applications have been generated. Such matrices are used to promote rapid cell growth, and can also be generated from the present inventive electronically active protein nanowires to include specific amino acid sequence growth factors. Although there has been interest in using protein fibers as biomaterials, effective production of engineered materials that have the desired dimensions and properties faces considerable technical challenges.

SUMMARY OF THE DISCLOSURE

The present disclosure provides protein materials with nanometer level of structure based on knowledge of self-assembly tendencies of α-helical proteins. Using these proteins as building blocks, oligomeric assemblies were created where α-helices assemble by taking advantage of hydrogen bonding and van der Waals' forces to gain stability. Cartilage oligomeric matrix protein (COMP) is the protein upon which the present invention is initially based. α-helical COMP assembles into a pentameric bouquet composed or of five equal subunits which arrange to form a coiled-coil structure. This protein is comprised of various domains. While not intending to be bound by any particular theory, it is considered that its ability to assume a pentameric structure is attributed to its N-terminal coiled-coil region, denoted COMPcc. Cysteine residues (positions 68 and 71) in COMPcc create interchain disulfide bridges between strands. Also, the COMP protein upon which the present inventive proteins are based has the cysteines mutated to serines (denoted COMPccS), in an effort to prevent oxidation. Further, two novel proteins of the present invention that are coiled-coils proteins derived from COMPccS (referred to as CC and Q54) have been engineered to generate fibers. Alone (as CC or Q54) and when combined, these proteins self-assemble via electrostatic interactions to form the longitudinally extending fibers of the present invention. These fibers have the ability to bind small molecules.

In one aspect, this disclosure provides protein materials comprising a plurality of homopentamers of a protein, where the protein monomeric units of the homopentamers may comprise the sequence of CC or the Q54 proteins as described herein. In one embodiment, the protein monomeric units have the sequence of SEQ ID NO:1 or SEQ ID NO:2. The homopentamers (as well as the individual protein units) form coiled-coil structures to form protofibrils (also referred to herein as fibrils) and several of the protofibrils may associate longitudinally to form nanofibers. In one embodiment, all the homopentamers forming the protofibrils and therefore the nanofibers are identical—being formed from the same protein, which, in one embodiment, is CC or Q54.

In one embodiment, the present disclosure provides protein materials comprising nanofibers, each nanofiber is made of a plurality of fibrils which comprise a plurality of self-assembled homopentamers of a protein. In one embodiment, the protein has the sequence of SEQ ID NO:1 (the CC protein) and in another embodiment, the protein has the sequence of SEQ ID NO:2 (the Q54 protein).

In one embodiment, the present disclosure provides protein materials comprising a plurality of homopentamers of a protein of SEQ ID NO:1 or SEQ ID NO:2, wherein the material is in the form of a film.

In one aspect, this disclosure provides a method for formation of protein nanofibers. The method comprises providing a mixture of the plurality of the monomer protein units and providing conditions such that self-assembly of the proteins occurs to effect the formation of the nanofibers.

The protein abbreviations used herein are as follows:
Q or Q54 (SEQ ID NO:1) is a variant of COMPcc.
C or CC (SEQ ID NO:2) is a variant of COMPcc.
L or L44 (SEQ ID NO:3) is a variant of COMPcc.
COMPcc (SEQ ID NO:4) is the coiled-coil region of COMP.
COMPcc$^s$ or COMPcc$^s$ wt is a variant of COMPcc, wherein the two cystines have been replaced with serines.
Qx (SEQ ID NO: 6) is a variant of Q54
Cx (SEQ ID NO:7) is a variant of CC.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 22a-22r. Confocal microscopy fluorescence images of several Q protein fibers in the presence of 50 µM curcumin at pH 4, 50 mM PB. Scale bars in (d), (k), and (l) represent 10 µm, (a)-(c) and (e)-(j) represent 20 µm, (b) and (l)-(o) represent 30 µm. Panels (p)-(r) originate from a single Z-slice (119 of 227) within the XYZ data set from panel (i). The image line profiles of the confocal (red trace) and interference contrast (black trace) resulting from the yellow sampling line are shown in panel (r), indicating the boundaries of the fiber and the curcumin fluorescence are coincident.

DETAILED DESCRIPTION OF THE DISCLOSURE

Figure 1:
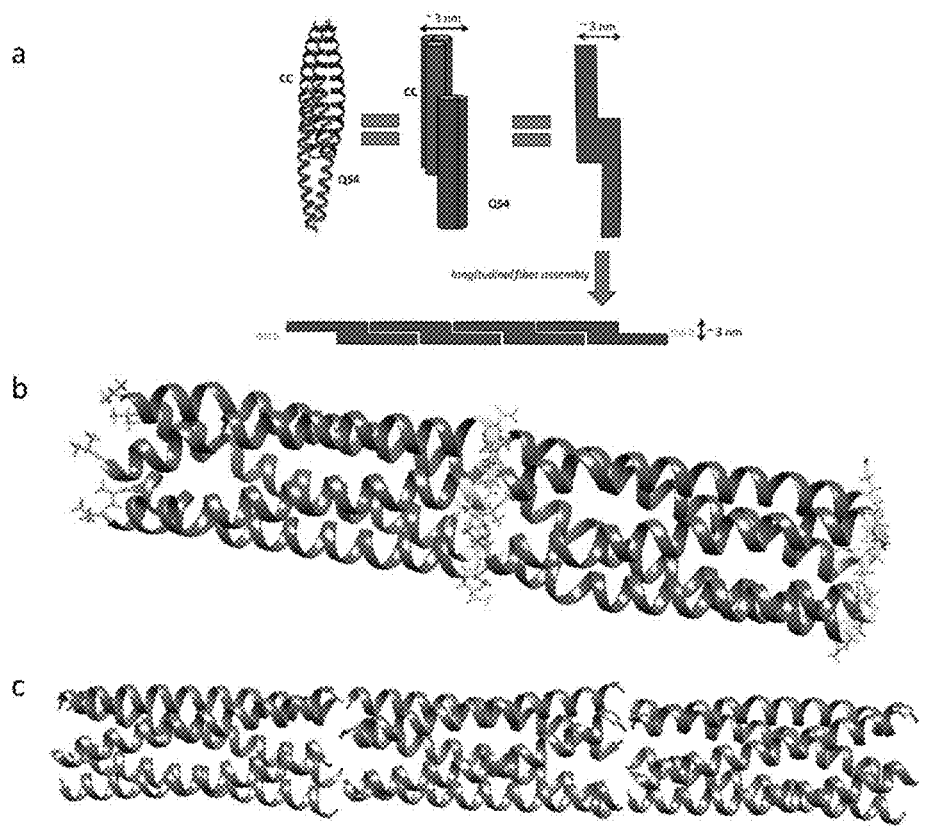
FIGS. 1*a*-1*c* show models of fiber assembly for hetero (FIG. 1*a*) and homo (FIG. 1*b* and FIG. 1*c*) assemblies of Q54 and CC arranged in pentamers for the present invention. These two proteins are derived from COMPcc (Protein database (PDB) file no. 1VDF).

The ability to rationally design proteins that are capable of acting as nanoscale structured scaffold materials is a powerful tool for a variety of applications, including for energy capture and storage and in biomedicine. Creating materials with this level of structure, in a manner that is reproducible at ambient processing conditions and with benign precursors, is a significant challenge for materials engineers and biosensor architects. Using biosynthetic techniques to generate biomaterials can improve upon structural, and therefore functional, properties of proteins and greatly increase the possibility for new design of functional materials. The present invention involves constructing nanoscale biomolecular materials in a reproducible manner.

The protein materials of the present invention have been designed with nanometer level of structure based on knowledge of self-assembly tendencies of α-helical proteins. Using these proteins as building blocks, we created oligomeric assemblies where α-helices assemble by taking advantage of hydrogen bonding and van der Waals' forces to gain stability. Each α-helix is defined by heptad residue repeats. α-helical proteins can assemble to form superstructures called coiled-coils, where the helices wind around one another with an overall left-handed twist. These assemblies contain structure-stabilizing interactions between hydrophobic residues and ionic interactions between charged residues. Interactions between coiled-coils have been used to aid rational design of protein fibers.

The cartilage oligomeric matrix protein (COMP) is found in cartilage, tendon, and ligament tissue (Gunasekar et al., *Biochemistry* 2009, 48 (36), 8559-8567). α-helical COMP assembles into a pentameric bouquet composed or five equal subunits which arrange to form a coiled-coil structure (Kajava et al., *Proteins: Structure, Function and Genetics*, 1996, 24, 218-226). This protein is comprised of various domains, but its ability to assume a pentameric structure is attributed to its N-terminal coiled-coil region, denoted COMPcc (Malashkevich et al., *Science* 1996, 274, (5288), 761-765). The pentamer is stabilized by electrostatic interactions between aligned heptad units, creating a 73 Å long hydrophobic core 2-6 Å in diameter between subunit chains, as was determined from the crystal structure. Cysteine residues (positions 68 and 71) in COMPcc create interchain disulfide bridges between strands. The COMP protein upon which the present proteins are based has the cysteines mutated to serines (denoted COMPcc$^s$) in an effort to prevent oxidation.

Two novel proteins that are coiled-coils proteins derived from COMPcc$^s$ (referred to as CC and Q54) have been engineered to generate fibers. When combined, these monomeric units of these proteins self-assemble via electrostatic interactions to form fibers that extend longitudinally.

In one embodiment, the present disclosure provides proteins, which have α-helical coiled-coil structures. The proteins, derived from COMPcc can self-assemble into homopentamers that can associate end to end to form fibrils and the fibrils in turn associate with each other longitudinally to form nanofibers.

In one aspect, the present disclosure provides protein structures comprising a plurality of homopentamers of a protein. The protein may be CC or Q54 protein. The protein structures may be in the form of nanofibers or may form other structures such as films, sheets, bundles, lattices and the like.

In one embodiment, the fibrils (protofibrils) formed by end-to-end association of homopentamers of the proteins have a diameter of from 1 to 10 nm (and all integers and ranges therebetween). In one embodiment, the diameter of the fibrils is from 2-5 nm and in one embodiment, it is 3.5 nm±0.5 nm.

The nanofibers are formed by association of the fibrils along their longitudinal aspect. In one embodiment, there are a plurality of fibrils in a nanofiber. In one embodiment, there may be from 10 to several thousands of fibrils in a nanofiber. In one embodiment, the diameter of the nanofiber is from 10 nm up to 1 micron. In one embodiment, it is at least 20 nm. It one embodiment, it is from 50 to 200 nm. In one embodiment, the diameter of the nanofibers is from 20 to 600 nm (including all integers therebetween and all ranges therebetween). The length of the nanofibers may be up to several microns. For example, the length may be between 1 to 30 microns and all integers and ranges therebetween. In one embodiment, the length is from 5 to 20 microns.

The present proteins form the coiled-coil structures over a wide range of pH and salt concentrations. For example, the pH may be from 3 to 10 (and all pH values to the tenth decimal place therebetween and all ranges therebetween). In one embodiment, the pH is from 3 to 8. In one embodiment, the pH is from 4 to physiological pH (i.e., 7.4). In one embodiment, the range for salt concentration (such as NaCl) concentration is 0-500 mM. In one embodiment, it is 0.01 to 500 mM.

The sequences of the two proteins of the present disclosure, which have been confirmed by amino acid analysis, are provided as SEQ ID NO:1 (for CC) and SEQ ID NO:2 (for Q54).

Buffers in which nanofibers may be formed include phosphate buffers of varying strength, ranging from 50-100 mM. Most favorable range of pH conditions for fiber formation is between 3 and 8 for Q and 6 and 8 for CC. Fibers may also be formed in buffers such as MOPS (3-(N-Morpholino)propanesulfonic acid or 4-Morpholinepropanesulfonic acid) and HEPES (4-(2-hydroxyethyl)-1-piperazineethanesulfonic acid). Ionic strength of the buffer solution can be increased by addition of NaCl, in the range of 0-500 or 0.01 to 500 mM salt (such as NaCl). In one embodiment, the pH range for formation of C fibers is between 6 and 8.

In one embodiment, the fibers may be formed as follows. Pure, denatured protein can be dissolved in a buffer of 6 M urea and dialyzed into 2 L volumes of buffer successively halving the urea concentration: from 3 M to 1.5 M to 0.75 M followed by 3×2 L volumes of buffer containing 0 M urea. Dialysis can be performed under conditions of constant mixing of the buffer (such as at 4° C. for a total of at least 36 h). Concentrations of phosphate buffer can be from 10-50 mM. Fibers readily form from pH 4-8.

The protein materials of the present disclosure may be used as scaffold materials for the construction of nanoelectronic materials as well as biomaterials for tissue engineering and biomedicine. These proteins can be further tuned to include unnatural amino acids and incorporate functional groups upon which inorganic materials can be templated. The specificity afforded by proteins—in their capability to self-assemble into fibers or bind with specific inorganic metals—makes them versatile, robust candidates for construction materials for advanced biosensors. By simply changing the amino acid chemistry of the protein's primary sequence, protein nanowires have been created with diameters on the nanoscale. The ability to fine tune physical parameters—including dimension and spatial arrangement and size of nanoparticle electronic elements—via chemical alteration permits such use.

The present protein materials may also be used for providing mesh or weaved materials, which may be useful for sequestration of agents or as scaffolds. The mesh or weaved materials may also be used as sieves for various filtration applications.

The method of present invention has the ability to generate fibers that vary in diameter. For another example, the instant inventive proteins are engineered to contain an unnatural amino acid, which imparts the ability to bioorthogonally attach any peptide to the protein fibers that can be used as a sensing element in biosensors.

The nanofibers of the present invention, in one embodiment, being composed solely of protein material, are inherently more biocompatible than prior polymers, even biodegradable polymers, while also having the ability to be further functionalized to bind metal nanoparticles. Thus, the protein-based nanofibers of the present invention are more biocompatible than current fibers, as proteins are natural components of human physiology.

The nanofibers of the present invention are made up of homopentamer subunits, which also contain a hydrophobic core or pore, affording the nanomaterials of the present invention the possibility to house small molecules, useful in applications such as drug delivery. The hydrophobic core or pore is a feature provided by the pentameric assembly of COMPcc derivatives.

In one embodiment, the nanofibers of the present invention are used to bind small molecules. It was observed that a much higher loading was achieved with the present nanofibers. For example, the molar ratio of small molecule to protein can be from 10:1 (including all ratios therebetween). In one embodiment, it is from 5 to 1.

The nanofibers of the present invention are cylindrical as opposed to hollow, being composed of several hundreds of smaller protofibrils. This increased proteins density may provide more robust material properties, such as conductivity. The nanofibers of the present invention exhibit diameters in a relatively smaller range, enabling them to exhibit more uniform physical properties.

The proteins of the present invention are longer than peptides used previously by others. The longer proteins of the present invention provide the opportunity to include binding sites for templation of metal nanoparticles and the ability to include other functional sequences on the protein. With longer sequences, the present invention provides protein nanofibers that afford the possibility to be further functionalized.

In one embodiment, by using the present methods, fibers that vary in diameter, may be generated. Additionally, as further described, proteins may be engineered to contain one or more unnatural amino acid, which can impart the ability to bioorthogonally attach any peptide to the protein fibers. The unnatural amino acid may be all the use of these nanofibers as a sensing element in biosensors.

The present proteins self-assemble into pentameric coiled-coil assemblies, and include a recognition sequence that enables them to self-assemble. We have observed fiber formation at concentrations as low as 2 μM. In one embodiment, the concentration of the composition is from 2 μM to 200 μM (including all integers and ranges therebetween).

Small hydrophobic molecules can be encapsulated in these pentameric coiled-coils. Some of these molecules include (but are not limited to) curcumin, all-trans-retinol, and vitamin D3, retinoid antagonists/inverse agonists, taxol, steroids, peptides, other anticancer and antiarthritis drugs, and the like.

In one embodiment, the present nanofibers comprise solely protein material. In one embodiment the nanofibers comprise solely a plurality of identical protein monomers. The protein monomers may be CC or Q54 proteins. The nanofibers are more biocompatible than polymers while also having the ability to be further functionalized to bind metal nanoparticles.

The nanofibers of the present invention comprise homopentamer subunits, which also contain a hydrophobic core, affording the nanomaterials of the present invention the ability to house small molecules, useful in applications such as drug delivery. The nanofibers of the present invention are cylindrical as opposed to hollow, as they comprise several hundred smaller protofibrils. This increased proteins density may contribute to their ability to bind to more small molecules uniformly and may also provide more robust material properties, such as conductivity.

In one aspect, this disclosure provides compositions comprising the protein nanofibers in a suitable carrier. For example, the carrier may be a suitable buffer, including a phosphate buffer with a pH of about 3 to 8. In one embodiment, the pH of the composition may be from 6 to 8.

In contrast to structures made from shorter peptides which do not provide the opportunity to include binding sites for templation of metal nanoparticles or the ability to include other functional sequences on the protein, the present proteins with longer sequences, form protein nanofibers that afford the possibility to be further functionalized.

The instant nanofibers can be used to form a film comprising a protein of the present invention and metal nanoparticles. The nanofibers are templates for metal nanoparticle formation. For example, the film has metal nanoparticles (e.g., gold nanoparticles) disposed in the film. In an embodiment, the metal nanoparticles are dispersed in the protein film. In an embodiment, the metal nanoparticles are dispersed in and on the protein film. In an embodiment, the film comprises a network of metal nanoparticles in a protein matrix. In an embodiment, the metal nanoparticles are monodisperse. The film can be formed by contacting the nanofibers with a metal nanoparticle precursor (e.g., a metal ion such as a gold anion (e.g., $AuCl_4^-$)) such that metal nanoparticles are formed and a film comprising the protein of the nanofibers having metal nanoparticles disposed therein is formed. For example, the metal nanoparticle precursor is a metal ion in a solution (e.g., a gold ion such as such $AuCl_4^-$ in solution). For example, the film is formed by contacting the nanofibers with a metal nanoparticle precursor (e.g., a reducible metal ion such as a gold anion (e.g., $AuCl_4^-$)) and a reducing agent (e.g., sodium borohydride) such that metal nanoparticles are formed and a film comprising the protein of the nanofibers having metal nanoparticles disposed therein is formed. In an embodiment, a method for making a film comprising a peptide of the present invention and nanoparticles comprises contacting nanofibers with a metal ions such that a film comprising the peptide of the nanofiber and metal nanoparticles formed from the metal ions is formed. In an embodiment, the nanofibers are contacted with metal ions and a reducing agent such that a film comprising the peptide of the nanofiber and metal nanoparticles formed from the metal ions is formed. In an embodiment, the present disclosure provides a protein film made by such a method.

In one embodiment, the present disclosure provides a protein film comprising a plurality of coiled-coil homopentamers of a protein, wherein the protein has a sequence of SEQ ID NO. 1 or SEQ ID NO. 2. The protein film may further comprise a dispersion of metal particles.

There are several foreseeable uses of the present invention. For example, the teachings of the present disclosure may be used to create compounds with predicted physical characteristics by designing them on a chemical level. Proteins that self-assemble to form fibers can be applied in areas other than nanoelectronics as well—the inherent biocompatibility of these materials makes them robust potential scaffold materials in tissue engineering applications. The effect that these materials will have as energy transfer or storage components will allow manufacturers of these advanced materials to reduce processing costs associated with raw materials and complicated production conditions. The development of natural materials with the same electronic capabilities as their synthetic counterparts will be of importance with a steady increase in the number of devices and sensors in use.

There are two main foreseeable commercialization paths for these types of protein nanofibers. The first is through large scale biosynthesis techniques, involving batch bioreactors for the growth of E. coli expression hosts in appropriate media. Subsequent protein purification can be performed on FPLC or a simple gravity flow column to generate large yields of pure protein. The second method for generating these proteins in large quantities is through chemical synthesis, or solid phase peptide synthesis (SPPS).

The invention is further described through the following illustrative examples, which are not intended to be restrictive.

Example 1

This example describes characterization of proteins CC and Q54. The proteins were characterized for assembly and structure using transmission electron microscopy (TEM), atomic force microscopy (AFM), scanning electron microscopy (SEM), fluorescence and confocal microscopy, zeta potential, dynamic light scattering, and circular dichroism. Circular dichroism curves show that the combination of CC and Q54 results in a very α-helical protein that is comprised of the assembly of both complementary proteins. The protein fibers have an average diameter on the order of 80 nm extending for several μm in length. Fibrils composing the fibers have a regular width of approximately 3 nm. In addition, fibers generated by CC and Q54 have been shown to be able to bind small molecules. The fluorescent molecule curcumin was bound to these protein assemblies and studied under fluorescence and confocal microscopes. Curcumin is known to bind within the hydrophobic pore formed by the homopentamer of COMPcc. The results of the experiments are described through a discussion of the figures.

FIGS. 1a-1c show models of fiber assembly for hetero (FIG. 1a) and homo (FIG. 1b and FIG. 1c) assemblies of Q54 and CC arranged in pentamers. In homoassemblies Q54 helices are shown in purple in FIG. 1b and CC are shown in gray in FIG. 1c, with valine residues in Q54 highlighted in cyan blue and glutamine residues in yellow to depict interaction. Models were compiled with PyRosetta.

Figures 2A, 2B:
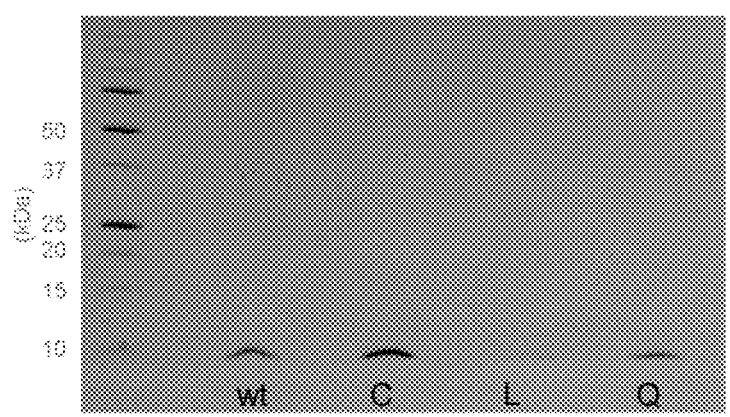
FIG. 2a shows sequence information for COMPcc$^S$ wt (SEQ ID NO: 4), CC (SEQ ID NO: 1), L44 (SEQ ID NO: 3) (also derived from COMPcc), and Q54 (SEQ ID NO: 2), from N-terminus to C-terminus for the present invention.
FIG. 2b shows the purified proteins on SDS PAGE.

FIG. 2a shows sequence information for COMPcc$^S$ wild type (wt), CC, L44, and Q54, from N-terminus to C-terminus. All proteins contain a flexible 6× His tag and several heptads. FIG. 2b shows SDS-PAGE gel with pure wt (6.9 kDa), CC, L44, and Q54 (6.3 kDa each).

Figure 3:
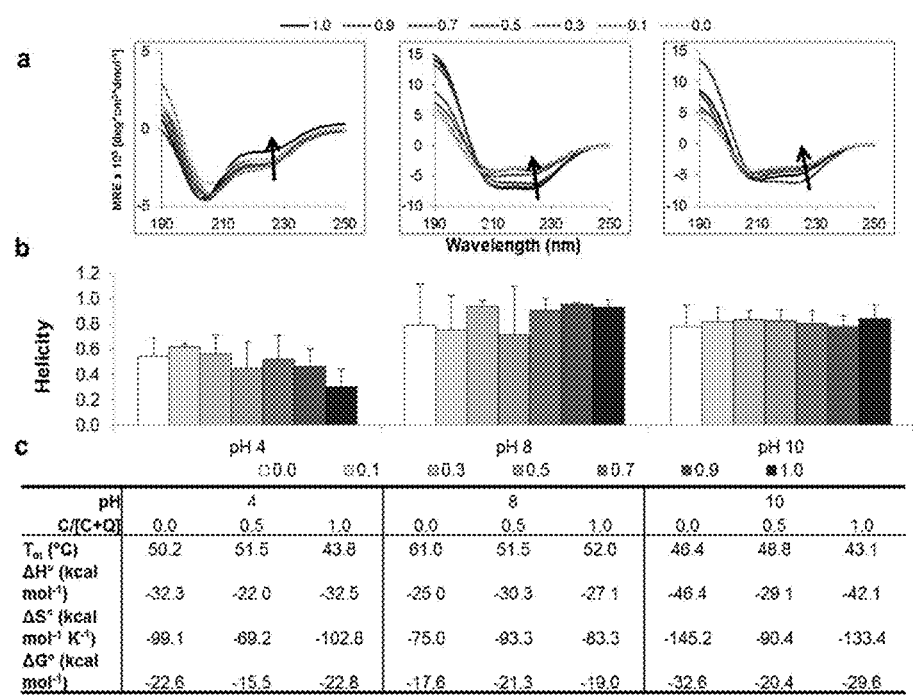
FIGS. 3a-3c show circular dichroism data for secondary structure analysis of CC, Q54, and mixtures thereof for the present invention.

FIGS. 3a-3c show circular dichroism data for secondary structure analysis of CC, Q54, and mixtures thereof. FIG. 3a shows wavelength scans for mixtures of CC and Q54 at pH 4, 8, and 10. At pH 4, deepest minima at 222 nm corresponds with equimolar mixtures of CC and Q54, while at higher pHs minima deepens as CC content is increased. Data is averaged from three replicates. FIG. 3b shows the ratio of θ at 222 nm to minimum θ from 195-210 nm for mixtures of CC and Q54 at pH 4. Data is averaged from three replicates with error bars representing the standard deviation. FIG. 3c shows thermodynamic constants obtained from thermal melts measured by circular dichroism. Melting temperature ($T_m$) is determined from thermal melts, and $\Delta H°$, $\Delta S°$, and $\Delta G°$ calculated through van't Hoff plots. Data is averaged from duplicate set of measurements.

Figure 4:
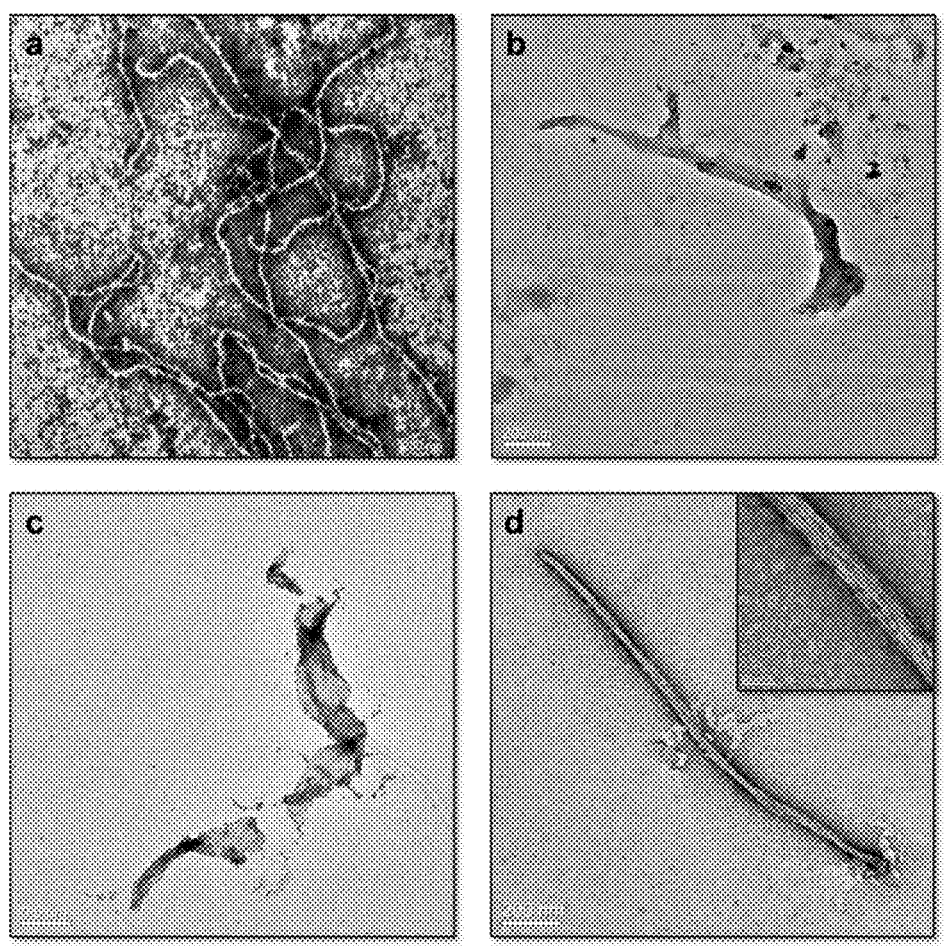
FIGS. 4a-4d show transmission electron micrographs of protein fibers and sheets for the present invention.
Figure 10:
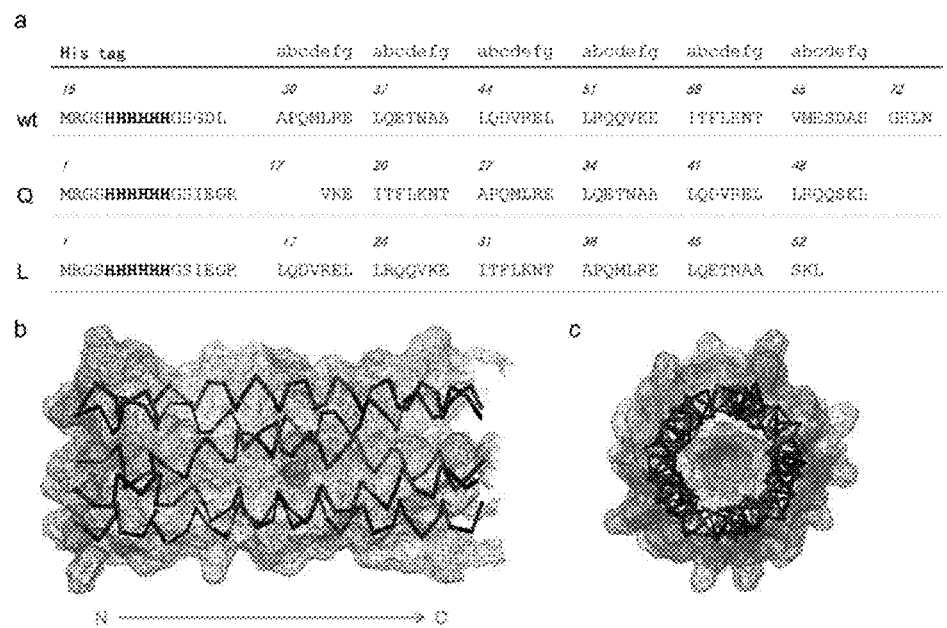

FIGS. 4a-4d show transmission electron micrographs of protein fibers and sheets. A fibrous network is formed by COMPcc wt at pH 8 as shown in FIG. 4a, 10 mM PB with fiber diameters measuring 17±3 nm. CC, shown in FIG. 4b and L44, shown in FIG. 4c, form sheet-like assemblies and larger aggregates at pH 4, 50 mM PB conditions. CC and L44 have not been observed to form fibers under these conditions via TEM. Q54, shown in FIG. 4d, regularly forms fibers with high levels of structure at pH 4, 50 mM PB, as can be seen by the protofibrils observed in the inset of FIG. 4d. Protofibril diameters for Q54 at these conditions have been measured to be in the range of 3-4 nm, where fiber diameters range from 50-100 nm. Q54 was found to form fibers over a wider range of pH than CC.

Figure 5:
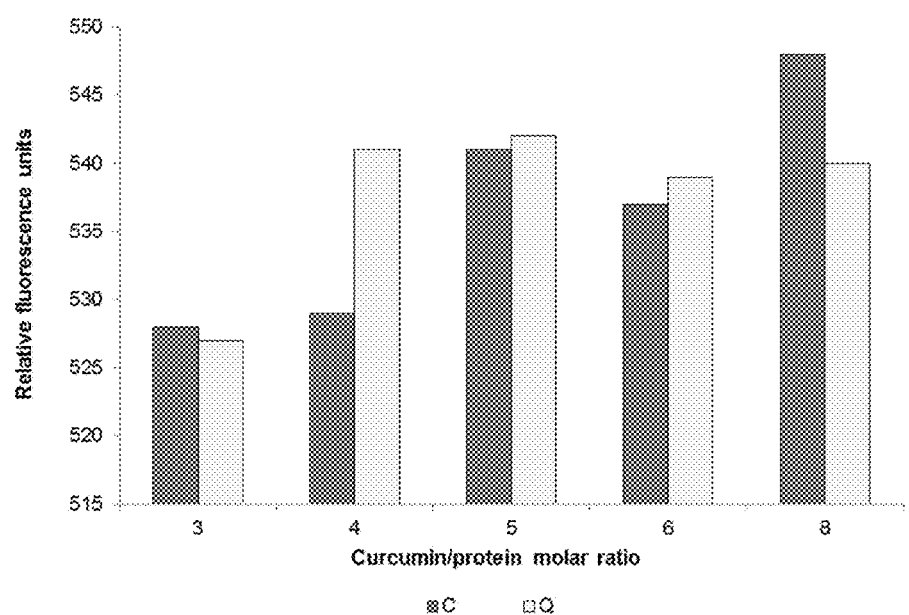
FIG. 5 shows relative fluorescence units at 540 nm for CC and Q54 with increasing concentrations of curcumin for the present invention.

FIG. 5 shows relative fluorescence units at 540 nm for CC and Q54 with increasing concentrations of curcumin Fluorescence values appear to increase up to a molar ratio of 5:1 curcumin:protein, above which they plateau. This indicated that this is a desirable binding ratio of small molecules to protein.

Figure 6:
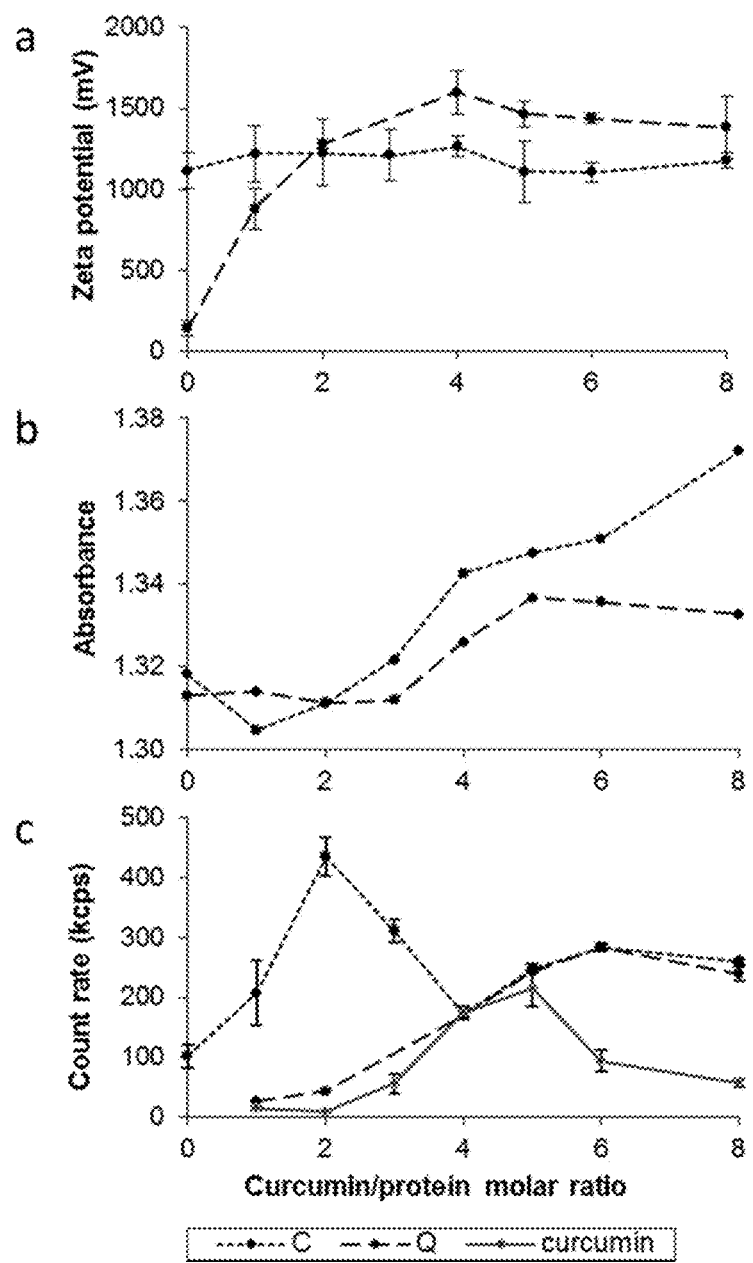
FIGS. 6a-6c show zeta potential (a), absorbance at 420 nm (b), and dynamic light scattering measurements of count rate (c) as a function of curcumin:protein molar ratio.

FIGS. 6a-6c show evidence of protein aggregation as concentration of curcumin is increased. FIG. 6a shows zeta potential increases as a function of increasing curcumin concentration for both CC and Q54. FIG. 6b shows absorbance measured at 420 nm as a function of curcumin concentration. As curcumin/protein molar ratio increases the absorbance increases correspondingly. FIG. 6c shows dynamic light scattering measurements of count rate increasing as a function of curcumin/protein molar ratio. Increase in count rate is indicative of aggregation.

Figure 7:
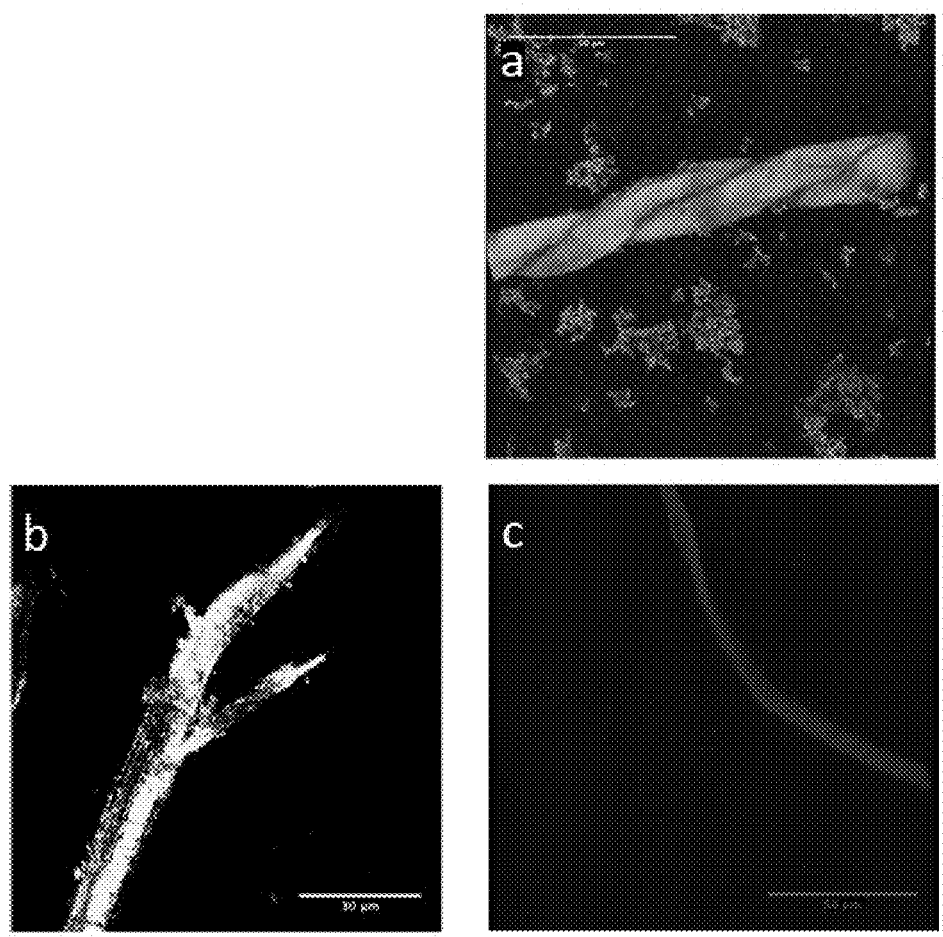
FIGS. 7a-7c. Confocal microscopy of Q54 (a), CC (b), COMPcc (c) in the presence of curcumin Mixture of protein to curcumin were all at a ratio 1:5. All protein samples were at 20 mM, to 100 mM curcumin.

FIGS. 7a-7c show confocal microscopy of CC, Q54, and COMPcc$^S$ wt, in the presence of curcumin. The mixture of protein to curcumin were all at a ratio of 1:5. All protein samples were at 20 mM, to 100 mM curcumin. All different proteins are in 50 mM phosphate buffer, pH 4. Protein and curcumin samples were combined and incubated for 12 hours prior to imaging. FIG. 7b shows that average width dimensions for imaged CC protein fibers was 19.24±2 μM. FIG. 7a shows Q54 protein fibers averaged 16.87±9 μM. The width of COMPcc$^S$ wt shown in FIG. 7c was determined to be 12.72 μm. No fibers were seen for L44. Overall, Q54 fibers appeared to be more uniform in width, as well as more robust and consistent in fiber formation.

Figure 8:
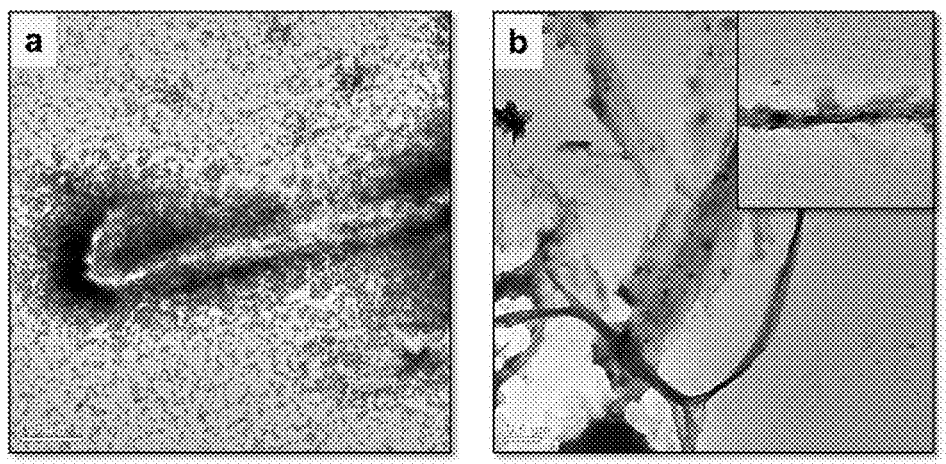
FIGS. 8a-8b show transmission electron micrographs of protein in the presence of curcumin, for CC (FIG. 8a) and Q54 (FIG. 8b).

FIGS. 8a-8b show transmission electron micrographs of protein in the presence of curcumin, at a molar ratio of 5:1 curcumin:protein at pH 4, 50 mM PB. Large aggregates were seen in both CC as shown in FIG. 8a and Q54 as shown in FIG. 8b. In FIG. 8b, several Q54 fibers appear to be aggregating together. The inset of FIG. 8b shows the protofibrils structure of the protein material seen in Q54 in the presence of curcumin Under the same conditions CC and Q54 have been seen to form large fibers via confocal. Although fibers with the same mesoscale dimensions observed in confocal were not seen, this was most likely because larger fibers were wicked away during sample preparation.

Figure 9:
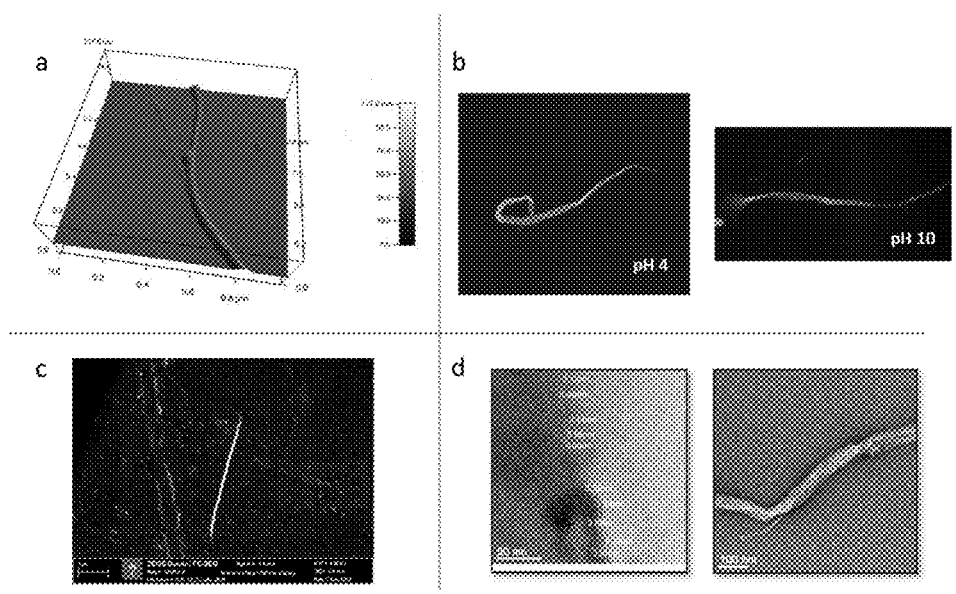
FIGS. 9a-9d show various forms of microscopy employed to study the morphology of the designed protein fibers of the present invention—a) atomic force microscopy; b) fluorescence microscopy; c) scanning electron microscopy; and d) transmission electron microscopy FIGS. 10a-10c. Protein sequences and surface charge representation for Q. (a) Sequence information for wt (SEQ ID NO: 4), Q (SEQ ID NO: 2), and L (SEQ ID NO: 3), from N-terminus to C-terminus, with the histidine tags in bold. Surface charge representation of Q pentamer under acidic conditions viewed along (b) and down (c) the pentamer axis.

FIGS. 9a-9d show various forms of microscopy have been employed to study the morphology of the designed protein fibers. FIG. 9a shows atomic force microscopy showing the fiber topography. FIG. 9b shows fluorescence microscopy where fluorescent molecule curcumin was bound to protein fibers at several pH values, indicating proteins' ability to bind small molecules. FIG. 9c shows scanning electron microscopy. FIG. 9d shows transmission electron microscopy of and equimolar mixture of CC:Q54 proteins, where individual protofibrils measuring ~3 nm can be seen. Thus, it appears that Q54 fibers form more readily than CC fibers. They are more thermodynamically stable (higher melting temperatures) and more robust.

Example 2

In this example, we describe the self-assembly of a novel protein (Q) designed by swapping regions of wt (COMPcc), and compare it to wt as well as a negative control swap protein, called L. Q assembled into robust nanofibers with unprecedented diameters up to 560 nm under pH 4. In the presence of the small molecule curcumin, the Q fibers further assembled into microfibers with diameter of 16 μm, akin to natural keratin and spider silk fibers measuring tens of micrometers in diameter, providing the first example of an engineered protein microfiber.

Materials

Sodium phosphate (monobasic and dibasic) and nickel-nitrilotriacetic acid resins were purchased from Sigma-Aldrich. Ampicillin, isopropyl-β-D-thiogalactopyranoside (IPTG), tryptone, urea, tris-HCl, and sodium chloride were obtained from Fisher Scientific. Yeast extract, methanol, and curcumin were purchased from Acros Organics and BCA kit was obtained from Pierce. Imidazole was purchased from Alfa Aesar and copper grids for TEM were purchased from Ted Pella.

Methods

Gene sequences for Q and L were generated via polymerase chain reaction (PCR) amplification and PCR assembly of DNA fragments of the wt COMPcc gene. Q was constructed by assembling Q1 and Q2, and L was constructed by the assembly of L1 and L2. Template DNA was COMPcc$^s$, whose gene sequence is provided in SEQ ID NO: 5. Primer sequences used to generate fragments for Q and L are provided in Table 1.

TABLE 1

| | Primer sequence (5' → 3') | SEQ ID NO: |
|---|---|---|
| L Fwd1 | GCATGGGATCCATCGAAGGTCGCCTGCAGGACGTTCGTGAAC | SEQ ID NO: 8 |
| L Rev1 | CATCTGCGGCGCGGTGTTTTTCAGGAAGG | SEQ ID NO: 9 |
| L Fwd2 | CTGAAAAACACCGCGCCGCAGATGCTGCGT | SEQ ID NO: 10 |
| L Rev2 | GCATGAAGCTTTGACGCCGCGTTGGTTTCCTG | SEQ ID NO: 11 |
| Q Fwd1 | GCATGGGATCCATCGAAGGTCGCGTTAAAGAAATCACCTTC | SEQ ID NO: 12 |
| Q Rev2 | GCATGAAGCTTTGACTGCTGACGCAGCAGTTC | SEQ ID NO: 13 |

The Q1 fragment was generated with the primers Q Fwd1/L Rev1 and Q2 with Q Fwd2/L Rev2. The L1 fragment was generated with the primers L Fwd1/L Rev1 and L2 with L Fwd2/L Rev2. Phire Hot Start II DNA polymerase enzyme (Thermo Scientific) was used in the PCR reactions described herein. Concentrations of the reagents used for PCR amplification of DNA fragments were: 0.7 μL (200 ng) COMPcc$^s$ template DNA, 10 μL (1×final concentration) reaction buffer (Agilent), 1 μL (0.2 mM) dNTPs (Roche), 1 μL dimethyl sulfoxide (DMSO) (Sigma), 1 μL (10 μM) respective forward primer, 1 μL (10 μM) respective reverse primer, 34.3 μL 2× filtered deionized water, and 1 μL Phire enzyme for a total reaction volume of 50 μL. The same protocol was used to amplify all DNA fragments: 98° C. for 2 minutes, [98° C. for 5 seconds, 54° C. for 5 seconds, 72° C. for 20 seconds] repeated for 30 cycles, 72° C. for 1 minute, and 4° C. until reaction tube was removed from PCR apparatus.

For electrophoresis of amplified DNA, 5 μL of dye was added to the 50 μL reaction tube and 15 μL of the sample was loaded into a 2% (1 g agarose (Fischer Scientific) in 50 mL 1×TAE buffer (Quality Biological)) agarose gel. The gel was run for 30 minutes at 100 V in 1×TAE buffer. DNA was purified from the gel using a ZYMO DNA purification kit (Zymo Research) suspended in 2× filtered deionized water. Concentrations were measured using the NanoDrop. The DNA for Q1, Q2, L1, and L2 was frozen at −80° C. for 15 minutes and lyophilized for 3 hours. DNA was then resuspended in 2× filtered deionized water to reach a concentration of 33 ng/μL for future use in PCR assembly experiments.

The DNA fragments for Q were generated through PCR assembly of Q1/Q2, and L was generated through assembly of L1/L2. Template DNA for generate Q was Q1 and Q2, where template to generate L was L1 and L2. For the generation of Q, primers Q Fwd1 and Q Rev2 were used, and primers L Fwd1 and L Rev2 were used to generate L. Concentrations of the reagents used for the first step of PCR assembly of Q and L DNA were: 3 μL (100 ng/μL) Q1 or L1 template DNA, 3 μL (33 ng/A) Q2 or L2 template DNA, 10 μL (1× final concentration) reaction buffer, 1 μL (0.2 mM) dNTPs, 1 μL dimethyl sulfoxide (DMSO), 29 μL 2× filtered deionized water, and 1 μL Phire enzyme for a total reaction volume of 50 μL. To anneal DNA fragments prior to PCR amplification the following protocol was used: 98° C. for 2 minutes, [98° C. for 2 minutes, 54° C. for 5 seconds, 72° C. for 20 seconds] repeated for 10 cycles, 72° C. for 1 second, and 4° C. until reaction tube was removed from PCR apparatus. Tubes were removed and 1 μL (10 μM) respective forward primer, 1 μL (10 μM) respective reverse primer were added to Q and L tubes. The same protocol was then used to amplify Q and L DNA: 98° C. for 2 minutes, [98° C. for 5 seconds, 54° C. for 5 seconds, 72° C. for 20 seconds] repeated for 35 cycles, 72° C. for 1 minute, and 4° C. until reaction tube was removed from PCR apparatus. The DNA sequences of the genes generated are listed in Table 2.

TABLE 2

DNA sequences for L and Q.

| DNA sequence (5' → 3') | SEQ ID NO: |
|---|---|
| L GGATCCATCGAAGGTCGCCTGCAGGACGTTCGT GAACTGCTGCGTCAGCAGGTTAAAGAAATCACC TTCCTGAAAAACACCGCGCCGCAGATGCTGCGT GAACTGCAGGAAACCAACAATCAAAGCTT | SEQ ID NO: 14 |
| Q GGATCCATCGAAGGTCGCGTTAAAGAAATCACC TTCCTGAAAAACACCGCGCCGCAGATGCTGCGT GAACTGCAGGAAACCAACGCGGCGCTGCAGGAC GTTCGTGAACTGCTGCGTCAGCAGTCAAAGCTT | SEQ ID NO: 15 |

For electrophoresis of amplified DNA, 5 μL of dye was added to the 50 μL reaction tube and 15 μL of the sample was loaded into a 2% (1 g agarose in 50 mL 1×TAE buffer) agarose gel. The gel was run for 30 minutes at 100 V in 1×TAE buffer. DNA was purified from the gel using a ZYMO DNA purification kit suspended in 2× filtered deionized water. Concentrations were measured using the NanoDrop. PQE30 plasmid vector containing an E. coli PheRS** mutation (Ala 294→Gly, The 251→Gly) and insert (Q or L) DNA were restricted prior to ligation. The contents of restriction reactions are given in Table 3.

TABLE 3

Contents of three reaction tubes used during restriction of PheRS** XLI blue vector DNA.

| Reagent | Q/μL | L/μL | PheRS**/μL |
|---|---|---|---|
| DNA | 11 | 11 | 2 |
| Buffer B | 5 | 5 | 5 |
| 2x MQ | 30 | 30 | 41 |
| BamHI | 2 | 2 | 1 |
| HindIII | 2 | 2 | 1 |
| TOTAL/μL | 50 | 50 | 50 |

The reaction tubes were incubated at 37° C. overnight to allow the reaction to go to completion. Restricted DNA was purified after electrophoresis and the concentration was measured using the NanoDrop. Purified and restricted Q and L were ligated to purified and restricted PQE30 PheRS** plasmid DNA. Positive (with insert) and negative (without insert) controls were prepared according to Table 4.

TABLE 4

Ligation reaction concentrations for ligating Q and L DNA with PQE30 PheRS** plasmid DNA.

| Reagent | −DNA control/μL | +DNA control/μL |
|---|---|---|
| Plasmid DNA | 2 | 2 |
| insert DNA | — | 5 |
| 2x MQ | 15 | 10 |
| T4 buffer | 2 | 2 |
| T4 ligase | 1 | 1 |
| TOTAL/μL | 20 | 20 |

T4 buffer and ligase were purchased from New England Biolabs. Reaction tube was incubated for two days and nights at 16° C. Ligated plasmid was then used for transformation. Transformation was performed for insert DNA/PheRS ligated plasmid vectors. Two reactions were prepared for each DNA type: (1) 5 μL DNA/PheRS DNA was added to 100 μL Zymo XL1 blue cells, and (2) 15 μL DNA/PheRS** DNA was added to 100 μL Zymo XL1 blue cells. Cells were kept on ice and thawed on ice for 30 minutes. After 30 minutes, 700 μL of Luria Bertani (LB) broth (at 37° C.) was added to each reaction, and was shaken at 350 rpm at 37° C. for 45 minutes. Cells were plated on tryptic soy agar (Teknova) plates with 0.2 mg/mL ampicillin (Amresco). Plates were incubated at 37° C. overnight. Bacterial colonies grown on TSA/ampicillin plates were obtained and starter cultures were grown in LB. The DNA from these cells was extracted through use of the MiniPrep kit (Zymo Research) and was purified. Purified DNA sequences of Q and L were confirmed (see Table S2) by sequencing by Eurofins MWG Operon.

Protein expression: Approximately 1 mL of starter culture was added to 1 L of Luria Broth (LB) containing 0.2 mg/mL ampicillin and incubated at 37° C., 250 rpm. After 9 hours, the cultures were induced with 0.2 mg/mL IPTG and incubated for 3 hours at 37° C., 250 rpm. Purification under denaturing conditions was carried out using 50 mM tris-HCl, 0.5 M NaCl, 20 mM imidazole, 6 M urea, pH 8 buffer. The soluble crude lysate was bound to Ni-NTA beads and allowed to equilibrate for 3 h at 4° C. The proteins were eluted with increasing gradient of imidazole (20 mM-1 M).

Pure fractions were refolded via stepwise dialysis in pH adjusted phosphate buffer (50 mM), halving the urea concentration successively. A BCA kit was used to estimate protein concentration with bovine serum albumin as a standard.

Circular dichroism: Circular dichroism (CD) measurements were conducted on a Jasco J-815 CD spectrometer. Wavelength and temperature scans were conducted with 10 μM ($6.3 \times 10^{-2}$ mg/mL) protein concentrations. The wavelength spectrum was measured over a range from 190 to 250 nm with a step size of 1 nm Mean residue ellipticity (MRE) was calculated from raw data according to the procedure described in Gunasekar et al. 2009. Secondary structure analysis of α-helical, β-sheet, and random coil content was calculated with the K2D method using DichroWeb software. Temperature scans of each protein were performed over a range of 20-85° C. with a temperature step of 1° C./min at 222 nm. Scans were also performed at of 2° C./min and 5° C./min to evaluate dependence of thermal melt signatures on scan speed. All measurements were made in duplicates of independently prepared proteins and data represents the average. Thermodynamic properties of wt and Q were determined through analysis of thermal melts. A two-state model was used, where assumptions included monophasic behavior and reversible melting behavior. These assumptions were confirmed experimentally by melting (from 20 to 85° C.) and cooling (from 85 to 20° C.) the proteins. Calculation of thermodynamic parameters including $T_m$, $\Delta G°$, $\Delta H°$, and $\Delta S°$ were performed according to the method described by Greenfield.

Transmission electron microscopy: A JEOL JEM-1400 transmission electron microscope (TEM) was used to study the supramolecular protein structure. Approximately 3 μL of 10 μM protein in 50 mM PB was spotted on copper grids. After 1 minute, the grids were blotted using filter paper and rinsed with 3-4 drops Milli Q water to remove excess salts from the buffer. After blotting with filter paper, the sample was negatively stained by adding 3 μL of 1% filtered uranyl acetate, blotted using filter paper, and dried at room temperature for 10-15 minutes. ImageJ software was used to measure the fibers dimensions.

Attenuated Total Reflectance Fourier Transform Infrared Spectroscopy (ATR-FTIR): ATR-FTIR experiments were performed using Perkin Elmer System 2000 FT-IR with DuraSamplIR II T diamond ATR accessory and equipped with a MCT-A detector. Approximately, 5 μL of peptide solution (10 μM in 50 mM PB, pH 4, 8, and 10) was added on the diamond ATR surface. The spectrum (128 scans) was measured at room temperature over a range of 4000-400 $cm^{-1}$ with 0.5 $cm^{-1}$ resolution. PeakFit software was used to process the data, which involved a $2^{nd}$ derivative zero baseline correction of the amide I region between 1700-1600 $cm^{-1}$ and deconvolution of peaks with a Gaussian function. All readings represent the average of two trials.

Zeta potential: Zeta potential measurements were performed on a Zetasizer Nano Series model Nano Z590. 50 mM phosphate buffer at pH 4 was used to saturate the clear polycarbonate disposable zeta cell DTS1060C prior to injecting 750 μL protein samples at protein concentrations of 10 μM. The following settings were used for zeta potential measurements in the DTS (Nano) software: 90° C. instrument settings, Smoluvchoski model, material protein, dispersant PBS, temperature of 25° C., viscosity 1.0200 cP, and dielectric constant of 1.34. Measurements were taken in triplicates, conducting 10 runs for each measurement, with a delay time of 2 seconds between each measurement.

Dynamic light scattering: Dynamic light scattering (DLS) measurements were performed on a Zetasizer Nano Series model Nano Z590. In measuring DLS, 50 mM phosphate buffer at pH 4 was used to wash the low volume disposable cuvette DTS0112 cell. Approximately, 750 μL of 10 μM protein sample with varying amounts of curcumin was then added to the cell. To measure size, the following settings were applied: material protein (refractive index 1.450), absorption 0.001, dispersant PBS with a viscosity of 1.0200 cP and refractive index of 1.335. Measurements were taken in triplicates, conducting 10 runs for each measurement, with a delay time of 2 seconds between each measurement.

Confocal microscopy: Samples were imaged using a Leica TCS SP2 AOBS confocal microscope system equipped with argon ion and HeNe lasers. A 63×/1.4 NA oil-immersion objective was used for all of the images. Lab-Tek II chambered #1.5 German coverglass system was used as the imaging slide. Curcumin was excited using the 458 nm line of the argon laser, and images were taken with the detection window set between 465 and 560 nm. The pinhole aperture was set at an Airy value of 1.0, which was equivalent to sampling an ~500 nm vertical z slice of the fiber, as estimated by the axial resolution, $r_{z,confocal} \approx 1.4 \lambda_{cm} n/NA^2$ (NA, numerical aperture; n, refractive index; $\lambda_{cm}$, emission wavelength (525 nm)). Interference contrast images were obtained using the Leica tube optics HC 1×/B apparatus with a focusing Bertrand lens. The 3D reconstructions were constructed using ImageJ 64 1.43 in concert with Amira 5.43, employing the Volren 3D rendering routine.

Nuclear magnetic resonance. 1 D $^1H$ nuclear magnetic resonance (NMR) was performed on a Bruker Ultrashield 500 Plus instrument and data was collected and analyzed using TopSpin 3.2 software. Protein concentrations were kept constant at 20 μM, with buffer conditions of 50 mM PB pH 4 with 1% (v/v) methanol and 1% (v/v) $D_2O$. NMR was performed in the absence and presence of curcumin, in a 5:1 molar ratio of curcumin:protein.

Results and Discussion

Design methodology: Here, we provide a new protein, Q (also referred to herein as Q54). The thermodynamic driving force for self-assembly of protein-based fiber structures consisted of optimal distribution of surface charges on the solvent-exposed outside of the homopentamer combined with shielding of the aliphatic residues within the pore of the protein oligomer. The results are discussed through a description of the figures.

FIGS. 10a-10c show the protein sequences and surface charge representation for Q. (a) Sequence information for wt, Q, and L, from N-terminus to C-terminus, with the histidine tags in bold. Surface charge representation of Q pentamer under acidic conditions viewed along (b) and down (c) the pentamer axis. Positive red patches in (b) and (c) are attributed to solvent-exposed lysine and arginine residues. Negative blue patches in (b) and (c) are attributed to solvent-exposed glutamate and aspartate residues. The wt consisted of a repeat of three leucines (L37, L44, L51) in the a site within the N-terminal pocket along with a valine (V47) in the d site of the adjacent helix, known to be indispensable for the formation of stable pentamers. The corresponding residues in Q became L34, L41, L48 and V44—all maintaining the same positions within the heptad. The extraneous last heptad of the wt protein was eliminated and the C-terminal portion after the glutamine residue at the d position was swapped to the N-terminus to better distribute the surface charge for lateral assembly, producing Q (FIG. 10a).

In order to compare structural and assembly characteristics of this engineered protein, we also designed a negative control, L, which was engineered to disrupt the N-terminal pocket crucial region for structure, stability, and pentamer formation by swapping at the leucine at position. Both the Q and L sequence was constructed via standard recombinant DNA methods and subsequently biosynthesized via bacterial expression followed by purification. As the design of Q and L focused on examining the effects of swapping the regions of wt, the proline residue that was present in the b position of wt was also in the engineered constructs. While proline is known as a helix breaking residue, its presence had a minimal effect on helical structure. Swapping of the N and C-terminal regions to generate Q and L result in proline being displaced to the center of the proteins, in positions 28 and 39 in Q and L, respectively.

Figure 14:
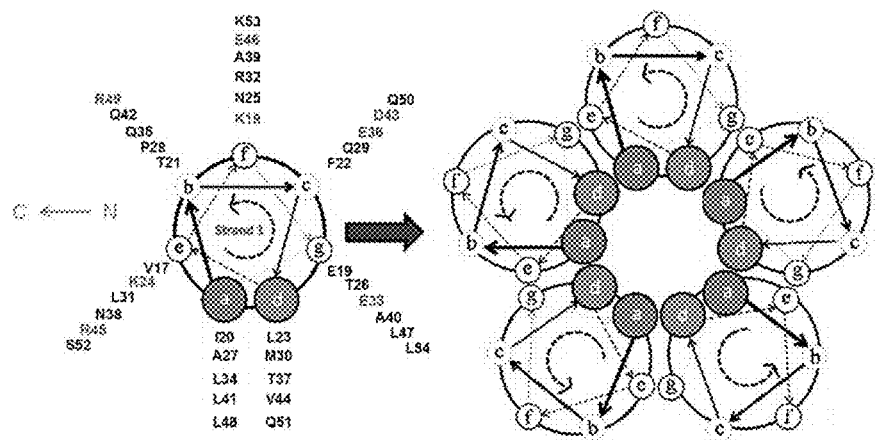
FIG. 14. Helical wheel for Q, showing the positioning of residues within heptad repeats. Residues highlighted in red contribute to positive surface charge, where residues highlighted in blue contribute to negative surface charge. Positive charge attributed to solvent-exposed lysine (K18 and K24, in the f and e positions, respectively) and arginine residues (R45 and R49, in the e and b positions, respectively). Negative charge attributed to solvent-exposed glutamine (E33, E36, and E46 in the g, c, and f positions, respectively) and asparagine residues (D43 in the c position). Individual α-helices self-assemble to form homomeric pentamers.
Figure 15:
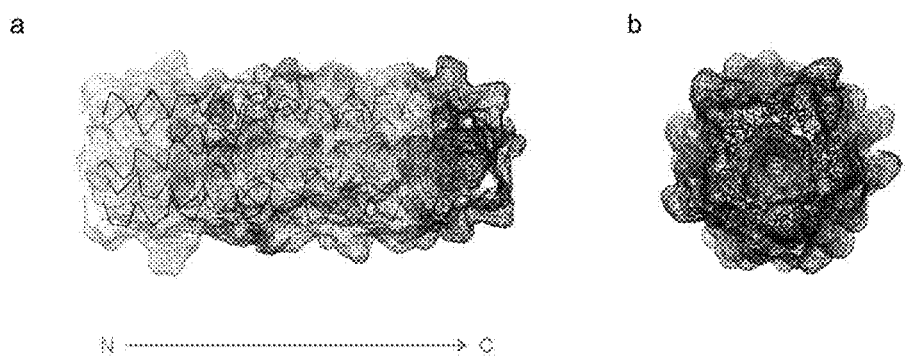
FIGS. 15a-15b. Protein sequences and surface charge representation for wt. Surface charge representation of wt pentamer viewed along (a) and down (b) the pentamer axis. Positive charge is represented in red, while negative charge is in blue.

The homopentameric assembly generated from Q subunits was visualized using Chimera. Electrostatic charge distribution in patches has previously been used to facilitate and direct self-assembly of coiled-coil protein fibers, confirmed by cryo-TEM, x-ray crystallography/diffraction, and modelling. The surface charge representation was generated by fully protonating the acidic residues in the software to best represent the charge distribution at acidic pH conditions (FIGS. 10b, 14, 15a, 15b). Red regions on the termini of the coiled-coil were positively charge as a result of solvent-exposed arginine and lysine residues, while the center of the pentamer was negatively charged due to solvent-exposed glutamine and asparagine residues (FIGS. 10b, 14). The overwhelmingly negative and positive "patches" that were produced along the length of the pentamer contribute to its ability to self-assemble. In contrast, surface charge distribution of wt did not show charged patches, but rather exhibited an overwhelmingly negative surface charge along the entire pentamer at acidic conditions (FIGS. 15a-15b).

Figure 11:
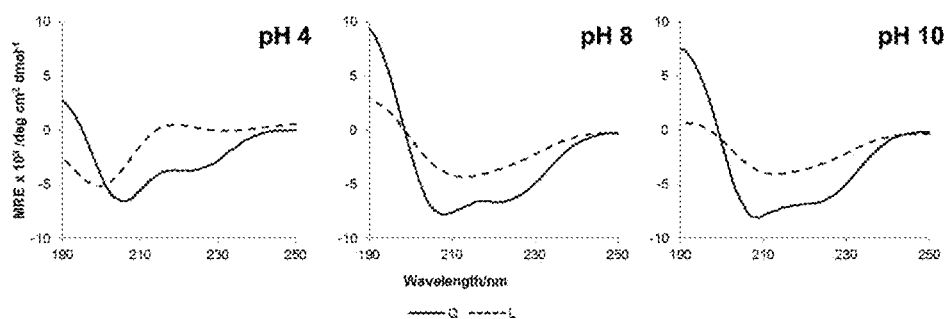
FIG. 11. Secondary structure of proteins at different pH conditions. Circular dichroism variable wavelength scans of Q (solid line) and L (dashed line) at pH 4, 8, and 10. Data is averaged from at least two replicates and was obtained with 10 µM protein concentration.
Figure 16:
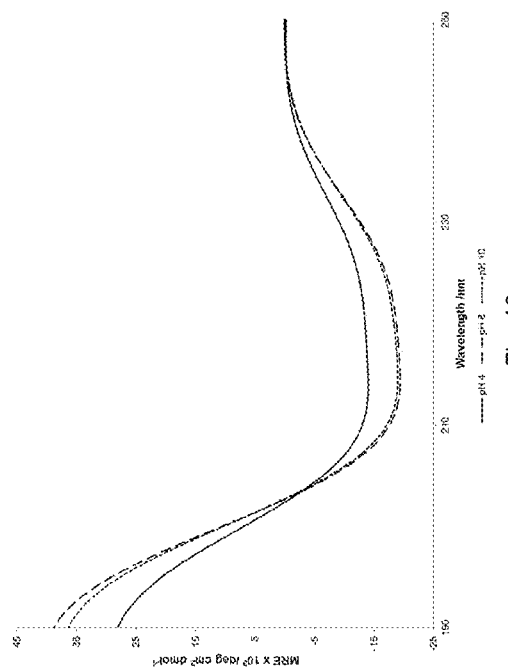
FIG. 16. Secondary structure of wt at different pH conditions. Wavelength scans of wt at pH 4 (solid line), pH 8 (long dashed line), and pH 10 (short dashed line). Data is averaged from three replicates.
Figure 17:
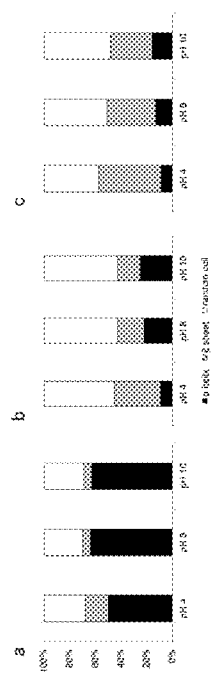
FIGS. 17a-17c. α-helical (black), β-sheet (grey), and random coil (white) content for (a) wt, (b) Q, and (c) L at pH 4, 8, and 10.
Figure 18:
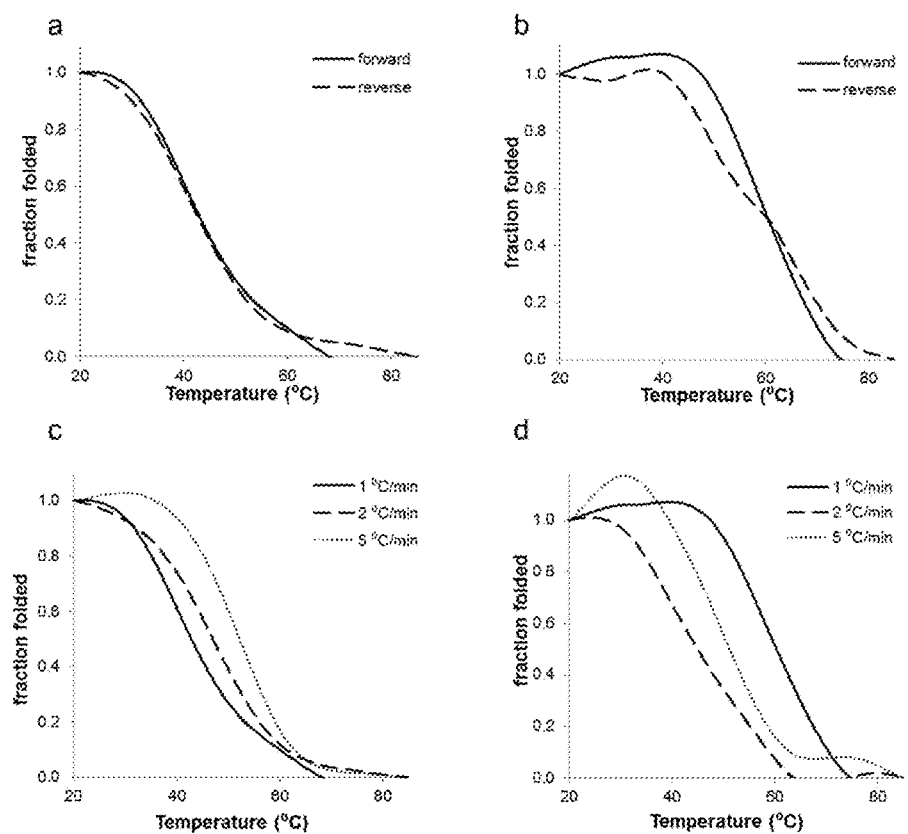
FIGS. 18a-18d. Thermal melt scans at 222 nm for wt (a) and Q (b) at pH 8. Melts were run in the forward, 20 to 85° C. (solid lines), and reverse, 85 to 20° C. (dashed lines), directions to confirm reversibility. Complete reversibility allowed for the van't Hoff analysis to be performed. Thermal melt scans at 222 nm for wt (a) and Q (b) at pH 8 at different scan speeds. Scan speeds of 1 (solid lines), 2 (dashed lines), and 5 (dotted lines) ° C./min were run in the forward direction for both proteins.

To assess the secondary structure of the proteins under acidic as well as neutral and basic conditions in solution, CD measurements were performed. While the removal of the peripheral heptad and reordering from wt led to a dampened signal, Q exhibited a helical signature with a double minimum of $-3.71 \times 10^3$ deg cm$^2$ dmol$^{-1}$ and $-6.54 \times 10^3$ deg cm$^2$ dmol$^{-1}$ at 222 nm and 206 nm, respectively (FIG. 11, Table 5). The presence of residue P28 towards the center of Q may have influenced the secondary structure, showing decreased helical content when compared to wt at pH 4 and 10 (FIG. 16). The negative control, L, was completely unstructured, devoid of helical content at pH 4 (FIG. 11). At neutral pH 8 conditions, Q revealed more helical structure (FIG. 11, Table 5, FIGS. 17a-17c). The negative control, L, did not illustrate α-helical structure at pH 8; rather it presented a single minimum at 213 nm (FIG. 11). At pH 10, Q maintained helical conformation with little change in the double minimum values, while L exhibited the same single minima (FIGS. 10a-10c, Table 5). While residue P39 in L may have contributed to a small loss in structure (as was seen in Q), the complete loss in helical structure across all pH conditions can be attributed to the disruption of the N-terminal pocket due to domain swapping. As the pH increased, the helical content of soluble Q protein increased. L exhibited a small increase in helical content from pH 4 to pH 10 and a moderate increase in random coil content.

Mean residual ellipticities from circular dichroism measurements at pH 4, 8, and 10 for wt, L, and Q. The data presented in Table 5 represents the average and standard deviation of at least two replicates.

TABLE 5

|  | pH 4 | | | PH 8 | | | pH 10 | | |
| --- | --- | --- | --- | --- | --- | --- | --- | --- | --- |
|  | wt | L | Q | wt | L | Q | wt | L | Q |
| $-\theta_{222} \times 10^3$/deg cm$^2$ dmol$^{-1}$ | 13.18 | −0.41 | 3.71 | 18.28 | 3.54 | 6.63 | 17.84 | 3.40 | 6.76 |
| $-\theta_{min} \times 10^3$/deg cm$^2$ dmol$^{-1}$ | 13.02 | 5.18 | 6.54 | 17.61 | 4.14 | 7.79 | 17.13 | 3.89 | 8.07 |
| α helices/% | 50 | 9 | 9 | 64 | 13 | 22 | 63 | 16 | 25 |
| β sheet/% | 18 | 49 | 36 | 6 | 38 | 21 | 6 | 32 | 18 |
| random coil/% | 32 | 43 | 55 | 30 | 49 | 57 | 31 | 52 | 57 |

Thermodynamic Properties:

Thermodynamic properties were assessed via thermal melt of the proteins at 222 nm. Prior to calculating thermodynamic constants, assumptions of monophasic behavior and melt reversibility were confirmed experimentally for wt and Q at all pHs by melting and cooling proteins (FIGS. 18a-18d). The van't Hoff equation was applied to thermal melts of the proteins in the range of 20-85° C. Overall, Q exhibited excellent stability across all pH values with melting temperatures (Tm) of 46.4-63.5° C. and Gibbs free energy (ΔG°) of −3.3, −3.8, and −3.1 kcal/mol at pH 4, 8, and 10, respectively. Thermodynamic constants obtained from thermal melts of 10 μM Q measured by circular dichroism are shown in Table 6.

TABLE 6

| pH | $T_m$ [° C.] | ΔH° [kcal mol$^{-1}$][a) | ΔS° [kcal mol$^{-1}$ K$^{-1}$][b) | ΔG° [kcal mol$^{-1}$][c) |
| --- | --- | --- | --- | --- |
| 4 | 55.3 | −32.3 | −97.1 | −3.3 |
| 8 | 63.5 | −32.6 | −96.8 | −3.8 |
| 10 | 46.4 | −46.4 | −145.2 | −3.1 |

[a)]van't Hoff enthalpy calculated as described in Supporting Information.

[b)]At equilibrium, ΔG° = 0. Hence, the change in entropy ΔS° = ΔH°/$T_m$.

[c)]Free energy of folding at 25° C. calculated according to the expression ΔG° = ΔH° − TΔS°.

As expected, thermal melts of L did not yield a significant enough gradient in the ellipticity at 222 nm to calculate thermodynamic properties. Compared to the parent wt, Q demonstrated a 7.2° C. and 14.7° C. increase in $T_m$ at pH 4 and 8, respectively, affirming that the modification made for the design of Q was indeed stabilizing (Table 7). At pH 10 the $T_m$ of Q and wt was essentially equal. Overall, Q was more stable at acidic and neutral pH conditions relative to wt, which could be attributed to the surface charge distribution along the pentamer subunits. Thermodynamic constants obtained from thermal melts of wt measured by circular dichroism are shown in Table 7.

TABLE 7

| pH | $T_m/°$ C. | $\Delta H°^{[a]}$/kcal mol$^{-1}$ | $\Delta S°^{[b]}$/kcal mol$^{-1}$ K$^{-1}$ | $\Delta G°^{[c]}$/kcal mol$^{-1}$ |
|---|---|---|---|---|
| 4 | 48.2 | −29.9 | −93.0 | −2.2 |
| 8 | 48.8 | −31.0 | −96.6 | −2.3 |
| 10 | 46.3 | −29.8 | −93.3 | −2.0 |

[a]van't Hoff enthalpy calculated as described in Supporting Information.
[b]At equilibrium, $\Delta G° = 0$. Hence, the change in entropy $\Delta S° = \Delta H°/T_m$.
[c]Free energy of folding at 25° C. calculated according to the expression $\Delta G° = \Delta H° - T\Delta S°$.

To determine whether Q could self-assemble into fibers, transmission electron microscopy (TEM) analysis was performed. While limited fiber formation was observed at neutral pH, an abundance of fibers was observed under acidic conditions as expected from our design (FIG. 12a, FIG. 16). The mechanism of protofibril bundling via self-assembly to form large, bundled fibers was the electrostatic charge distribution throughout the Q pentamers.

Figure 12:
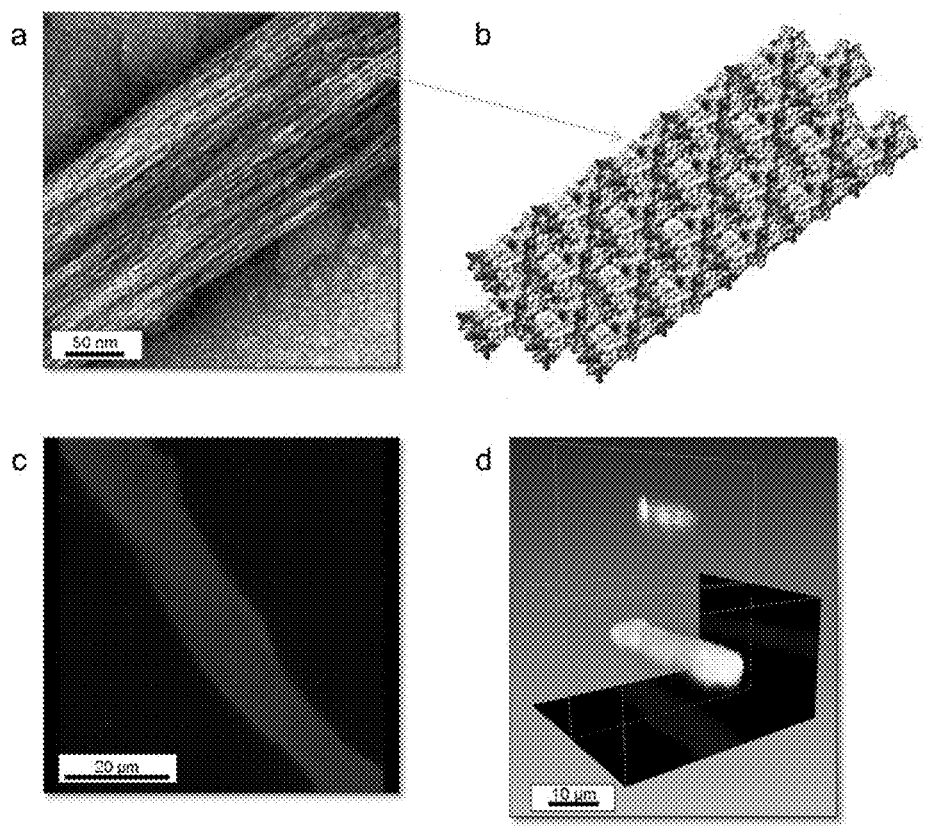
FIGS. 12a-12d. Microscopy and modeling of protein fibers. (a) Transmission electron micrograph of Q fiber, 10 µM, pH 4. (b) Schematic representation of Q fiber assembly with staggered positive (red) and negative (blue) regions of the pentamer. (c) Reconstruction of 3D confocal XYZ data of 10 µM Q protein in the presence of 50 µM curcumin (1:5 molar ratio of protein:curcumin) (d) 3D representation of the same Q fiber showing XZ and YZ orthogonal views and an oblique slice cross section above the 3D bounding box. Scale bars in (a), (c), and (d) represent 50 nm, 20 µm, and 10 µm, respectively.

Transmission electron micrographs of Q displayed the presence of bundled protofibrils forming high aspect ratio fibers (FIG. 12a). These protofibrils possessed diameters of 3.5±0.5 nm (n=210), which corresponded to the projected lateral dimension of pentameric helical bundles (FIG. 12b). Note that the model shown in FIG. 12 was an assumption based on the patched distribution of Coulombic surface charge in Q, with X-ray diffraction and cryo-TEM experiments underway. TEM data confirmed the diameters of protein fibers varied from tens to hundreds of nanometers (20-560 nm, n=14, FIGS. 19a-19q). At the upper limits, these fibers displayed tremendous lateral assembly of hundreds of protofibrils and thus larger than other de novo designed coiled-coil protein fibers to date. While wt demonstrated fiber formation (FIG. 16), the fibers are known to possess diameters on the range of 10-15 nm without any evidence for protofibrils. The L negative control revealed non-fibrous aggregates affirming that α-helical conformation was indeed important for fiber assembly (FIG. 16).

To quantifying the secondary structure of the protein in its solid-state, ATR-FTIR experiments were conducted to evaluate secondary structure of insoluble Q fibers at pH 4, 8, and 10 (Table 8). The frequency measured in the regions of the amide I and amide II absorptions of a protein correlate to the secondary structural motifs within the protein, and were thereby used to assess conformation of the protein in its solid-state (FIGS. 20a-20d). Secondary structure conformation based on ATR-FTIR data for Q in 50 mM PB at pH 4, 8, and 10, and in the presence of curcumin at a 5:1 molar ratio with Q at pH 4 are shown in Table 2. Percent composition was determined from relative areas of peaks fit to spectra (FIGS. 20a-20d).

TABLE 8

| | | % composition | | | |
|---|---|---|---|---|---|
| Conformation | Wavelength (cm$^{-1}$) | pH 4 | pH 8 | pH 10 | curcumin |
| β sheet | 1625-1640, 1675-1695 | 38 | 37 | 32 | 10 |
| Random coil | 1640-1648 | — | — | — | 12 |
| α helix | 1648-1660 | 62 | 63 | 68 | 79 |

Positions of amide I peaks in deconvoluted IR spectra of coiled-coil proteins are known to differ compared to peak locations arising from purely α-helical, monomeric proteins. Deviations are related to pitch values of the α-helices within the coiled-coils, with dimers showing the largest deviation (corresponding to helix deformations) and higher order oligomeric coiled-coils more closely resembling α-helical proteins. Our data correlate well with these observations, as the significant peak weights lie near the classical α-helical band position of 1650-1653 cm$^{-1}$ (FIGS. 20a-20d). ATR-FTIR measurements of Q at pH 4 results in a helical content of 62%, with helicity increasing to 63 and 68% at pH 8 and 10, respectively (Table 8). This trend of increasing helical content with increasing pH is consistent with the CD data. Solid-state ATR-FTIR data of Q secondary structure confirmed structured fibers visualized in TEM are indeed α-helical.

Curcumin binding: In the protein Q, the hydrophobic pore was maintained to enable binding to small molecules. The polyphenolic compound curcumin, has long been used for many therapeutic purposes due to its antiproliferative, antibacterial, and anti-inflammatory properties, but exhibits limitations in delivery methods due to its low solubility in aqueous solutions. In addition, curcumin induces aggregation of protein fibers, such as collagen and the acidic α-helical intermediate of PrP, a precursor to amyloid fibers. Thus, we incubated Q with varying concentrations (0-80 μM) of curcumin at pH 4 in order to study its overall binding ability and effects on protein morphology, charge, and aggregation.

Secondary structure in the presence of curcumin: Circular dichroism measurements reveal that the conformation of Q is not disturbed upon interaction with curcumin. In fact, the absolute value of the MRE value at 222 nm, an indicator of helicity, of Q increased linearly with increasing concentrations of curcumin (FIGS. 20a-20d). In addition, ATR-FTIR measurements were performed in the presence of a 5:1 molar ratio of curcumin to protein at pH 4. As can be seen in (Table 8), α-helical composition of insoluble protein fibers increases dramatically upon the addition of curcumin, going from 62% to 79% at pH 4. The ATR-FTIR spectra are particularly telling in this case (FIGS. 20a-20d), where spectra collected in the presence of curcumin demonstrate a very large, sharp peak of high intensity at 1653 cm$^{-1}$. These results indicate a stabilization of coiled-coil assembly in the presence of curcumin.

Macromolecular Assembly

Figure 19:
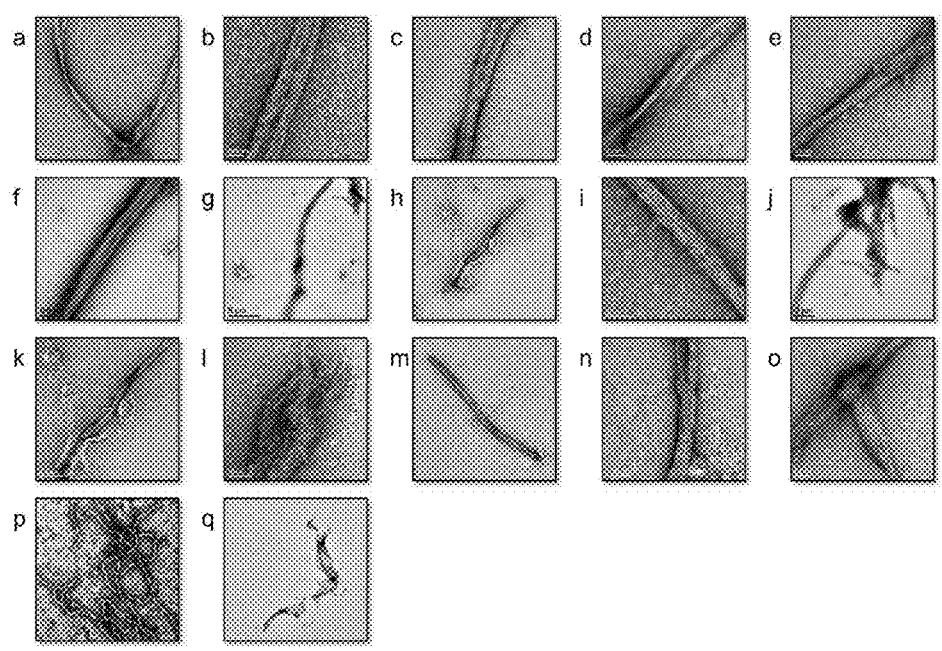
FIGS. 19a-19q. Transmission electron micrographs of protein fibers and sheets. Transmission electron micrographs Q protein fibers at pH 4, 50 mM PB (a)-(o). A fibrous network is formed by wt (p) at pH 8, 10 mM PB. L (q) forms sheet-like assemblies and larger aggregates at pH 4, 50 mM PB conditions. Scale bars in (a), (d), (e), (l), (o) represent 50 nm, in (b), (c), (i), and (n) represent 100 nm, (m) and (p) represent 200 nm, (f), (h), (k), and (q) represent 0.5 µm, (j) represents 2 µm, and (g) represents 5 µm.
Figure 20:
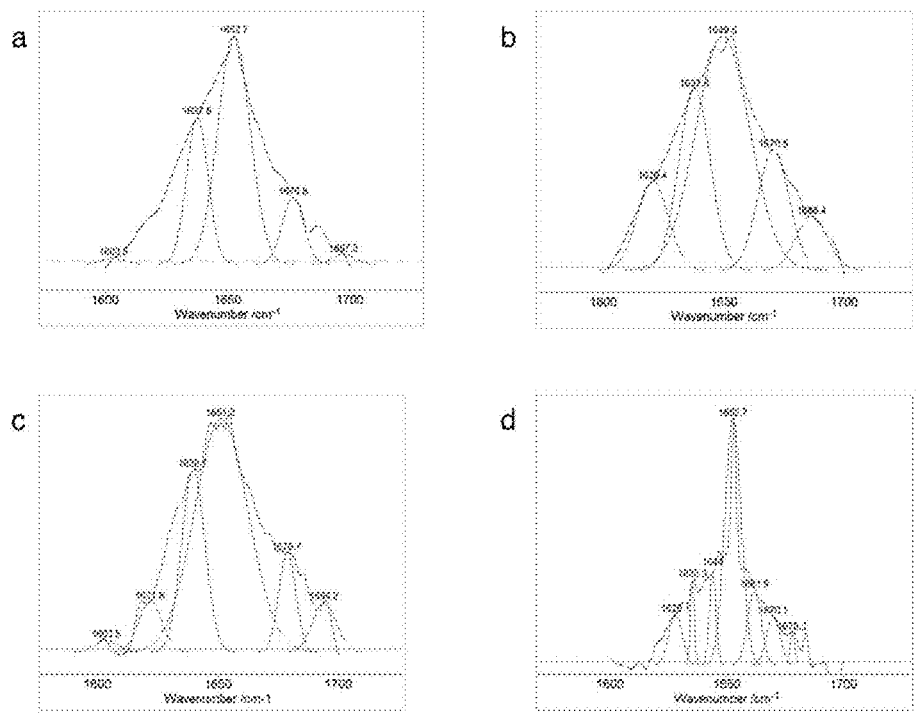
FIGS. 20a-20d. Fourier transform self-deconvoluted spectra of Q in 50 mM PB pH 4 (a), 8 (b), and 10 (c), and in the presence of curcumin at a 5:1 molar ratio at pH 4. Each spectra represents the average of two trials. ATR-FTIR measurements resulted in higher α-helical compositions at all pH conditions compared to CD due to the fact that the insoluble α-helical protein fibers cannot be measured by CD but can be detected by ATR-FTIR in solid-state measurements. Peaks were also detected in the regions pertaining to parallel and antiparallel β-sheets, with β-sheets making up the remaining fraction of the composition. Peaks corresponding to random coils were negligible.
Figure 23:
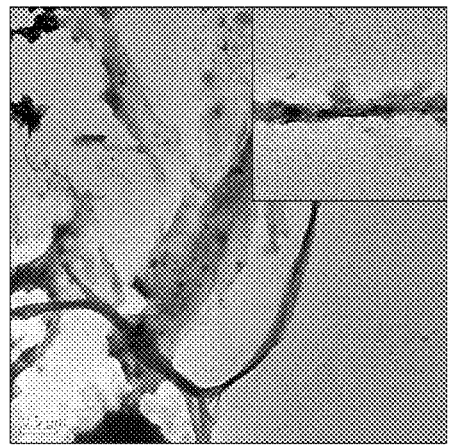
FIG. 23. Transmission electron micrographs of 10 µM Q in the presence of 50 µM curcumin (molar ratio of 5:1 curcumin:protein) at pH 4, 50 mM PB. Large aggregates were seen. Scale bars represent 0.5 µm.
Figure 24:
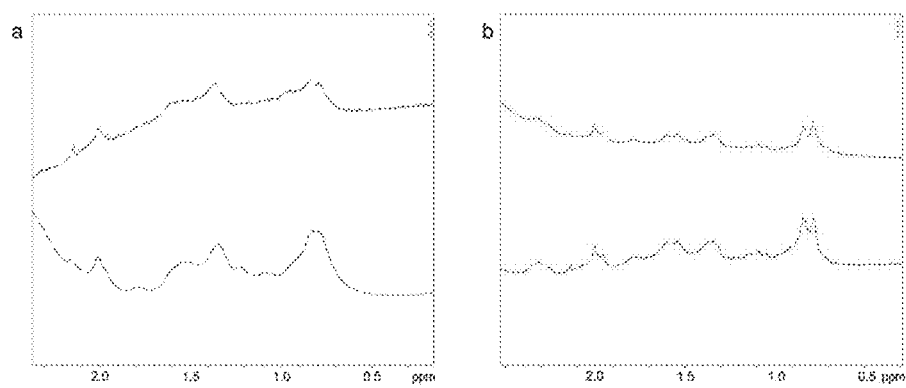
FIGS. 24a-24b. 1D 1H nuclear magnetic resonance scans for wt (a) and Q (b) in the absence (blue curves) and presence (red curves) of 100 µM curcumin (5:1 molar ratio of curcumin:protein). All protein concentrations were kept constant at 20 µM. Buffer conditions were 50 mM PB pH 4 with 1% (v/v) methanol and 1% (v/v) $D_2O$. These protein fibers, both with and without curcumin, are not completely soluble but not crystalline and the methods commonly used to determine protein structure, e.g. nuclear magnetic resonance, provide a limited scope of data to interpret.
Figure 25:
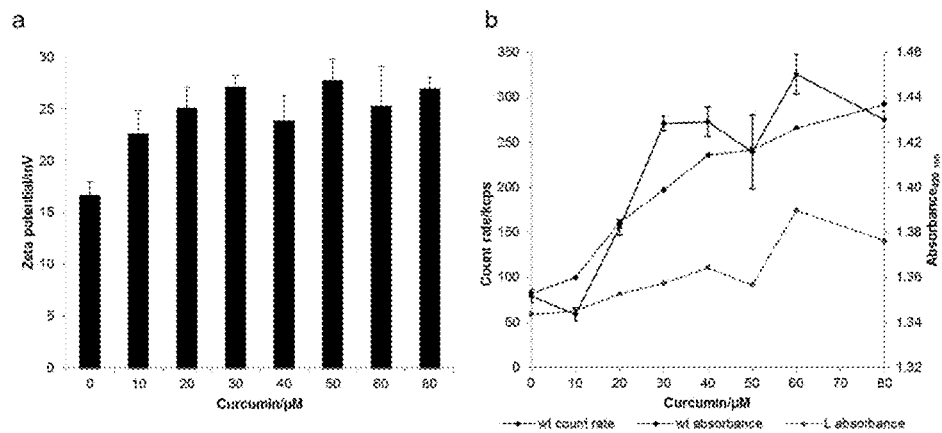
FIGS. 25a-25b. Aggregation of wt as a result of curcumin (a) Zeta potential increases slightly as a function of increasing curcumin concentration for wt. (b) Count rate and absorbance at 420 nm versus curcumin concentration. Absorbance measured at 420 nm as a function of curcumin concentration. As curcumin/protein molar ratio increases the absorbance increases correspondingly. Error bars in figures (a) and (b) represent an average of three trials.
Figure 26:
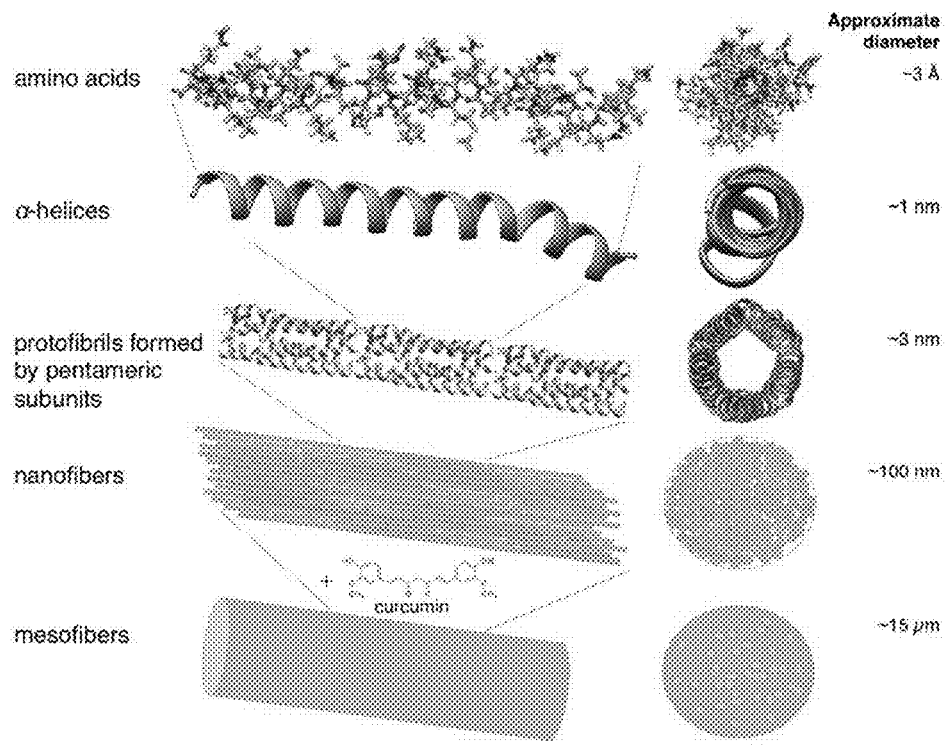
FIG. 26. Schematic for fiber assembly. Schematic representation of fiber assembly of Q on various length scales Amino acids form α-helices which assemble to form pentamers with approximate diameters of 3 nm Protofibrils are formed by assembly of pentameric subunits and bundle together to create protein fibers ranging from tens to hundreds of nm in diameter, and upon addition of curcumin mesofibers with diameters on the micrometer scale are generated.
Figure 27:
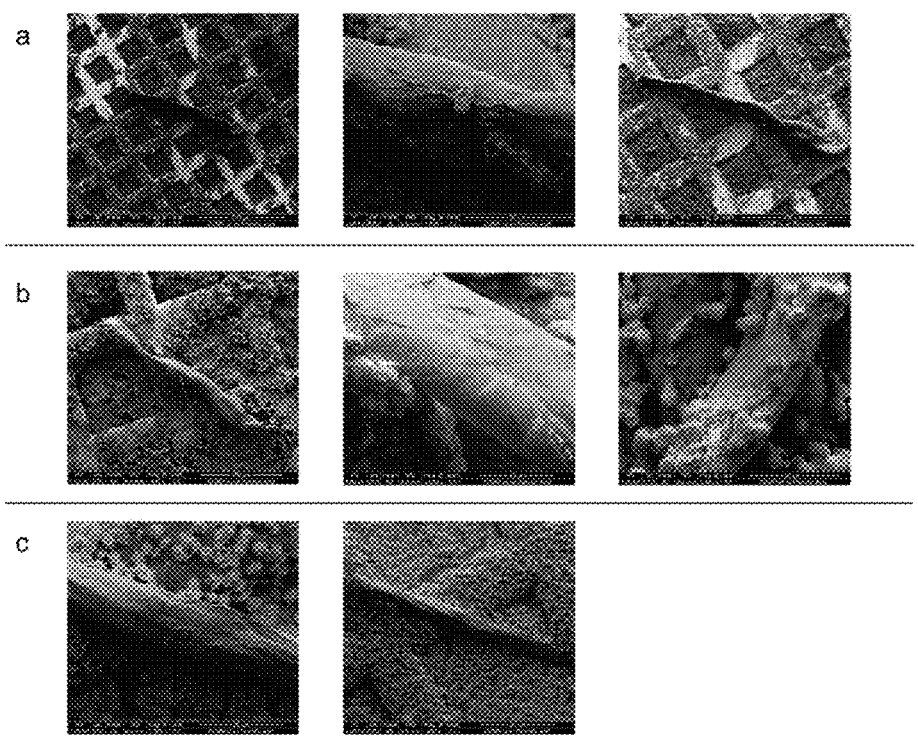
FIGS. 27a-27c. Scanning electron micrographs of proteins C (a), wt (b), and Q (c) in the presence of palmitic acid. For (a): from left to right, (1) scale bar=300 µm, magnification=156×, (2) scale bar=30 µm, magnification=1928×, (3) scale bar=200 µm, magnification=287×. For (b): from left to right, (1) scale bar=100 µm, magnification=442×, (2) scale bar=10 µm, magnification=4026×, (3) scale bar=20 µm, magnification=2446×. For (c): from left to right, (1) scale bar=20 µm, magnification=263×, (2) scale bar=50 µm, magnification=800×.
Figure 28:
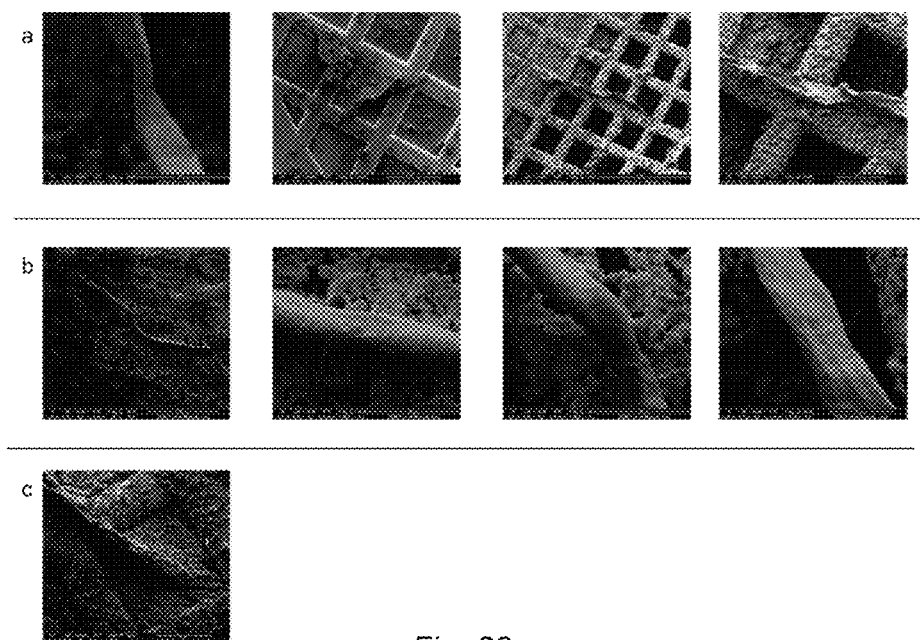
FIGS. 28a-28c. Scanning electron micrographs of proteins C (a2-4), wt (a1) and (b), and Q (c) in the presence of myristic acid. For (a): from left to right, (1) scale bar=30 µm, magnification=2062×, (2) scale bar=100 µm, magnification=372×, (3) scale bar=300 µm, magnification=203×, (4) scale bar=50 µm, magnification=625×. For (b): from left to right, (1) scale bar=200 µm, magnification=247×, (2) scale bar=30 µm, magnification=2062×, (3) scale bar=30 µm, magnification=2062×, (4) scale bar=20 µm, magnification=2154×. For (c), (1) scale bar=50 µm, magnification=743×.

As curcumin bound to structured protein exhibits fluorescence, confocal microscopy was performed on the Q•curcumin complex (FIGS. 12c and d). Surprisingly, microfibers were observed with an average diameter of 16.0±5.6 μm (n=22) (FIGS. 12c and 12d, FIGS. 19a-19q) indicating that the presence of curcumin further promotes fiber assembly. TEM was also used to study aggregation of Q as a result of curcumin (FIG. 23). Given the size of the large aggregates visualized in confocal, however, fibers of this dimension were not easily visualized via TEM as they did not adhere to the surface of the TEM grids and were easily wicked off when drying and preparing the samples. More importantly, curcumin was found distributed homogeneously throughout the fiber (FIG. 12d), and furthermore, the interference contrast boundaries of the fibers coincided with the curcumin emission boundaries in the confocal images (FIGS. 19a-19q). NMR experiments confirmed peaks between 0-2 ppm, a region pertaining to aliphatic residues within the protein and one that rarely exhibits signals from organic molecules. Peak broadening was demonstrated in the presence of curcumin in a 5:1 molar ratio of curcumin protein (FIGS. 24a-24b). These results suggested that curcumin was interacting with the nonpolar, hydrophobic residues located within the pore of wt and Q pentamers, however, did not preclude the possibility that curcumin could also be binding between the protofibrils. Fluorescence distributions from confocal measurements indicated that curcumin could be binding between protofibrils, contributing to observed aggregation effects. NMR and confocal data revealed that curcumin likely bound within the coiled-coil pore in addition to the surface of the pentamers, promoting supramolecular assembly.

Figure 13:
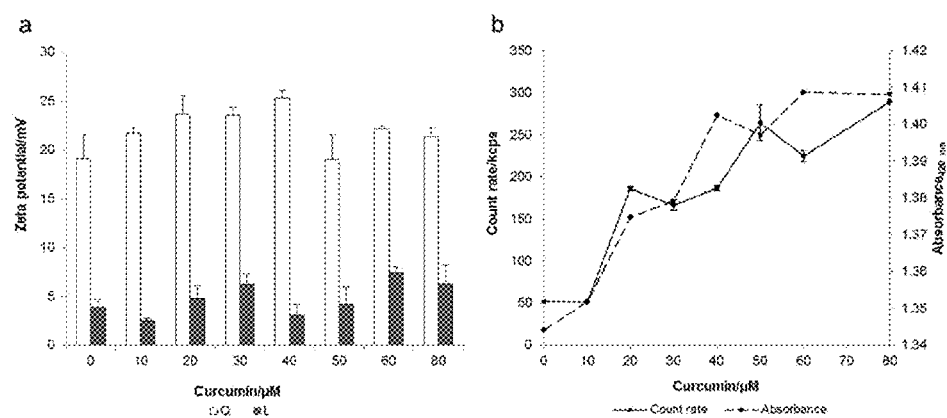
FIGS. 13a-13b. Aggregation of Q protein fibers due to increasing curcumin concentration. Protein concentration was held constant at 10 µM for zeta potential and DLS measurements. (a) Zeta potential as a function of curcumin concentration for Q (white bars) and L (grey bars). (b) Dynamic light scattering measurements of count rate for Q (solid line) as a function of curcumin concentration. Count rate was not obtained for L as signal at all curcumin concentrations was too low for detection. Absorbance measured at 420 nm as a function of curcumin concentration for Q (dashed line). Error bars in figures (a) and (b) represent an average of three trials.
Figure 21:
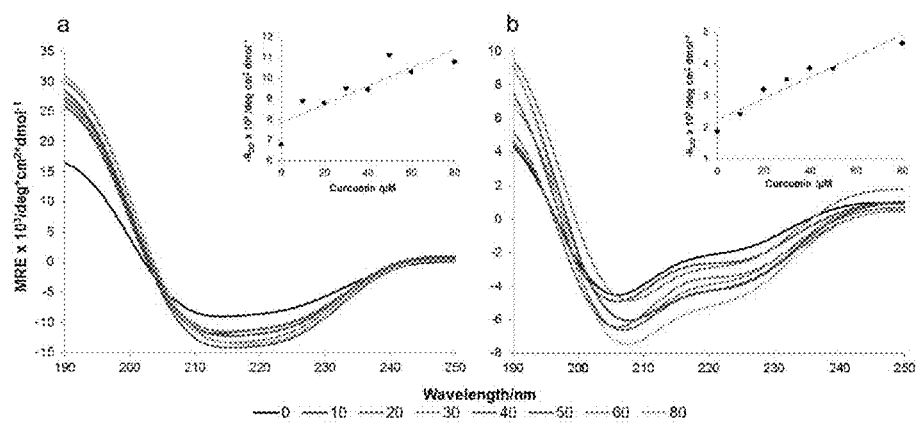
FIGS. 21a-21b. Helicity of wt and Q increase as a result of increasing curcumin concentration, pH 4 50 mM PB. Circular dichroism wavelength scans of (a) wt and (b) Q with varying molar ratios of curcumin Legend represents curcumin concentration in µM. Inserts show relationship between negative MRE at 222 nm of the mixtures with increasing curcumin/protein molar ratio, displaying near linear fits over the examined range.

To further characterize the assembly and aggregation caused by the addition of curcumin, zeta potential, count rate, and absorbance at 420 nm of protein is studied (FIGS. 13a-13b). Since curcumin is fully protonated at pH 4, the interaction of curcumin with negative charges on the protein is likely. Indeed, as curcumin concentration increases, the zeta potential exhibits a slight increase as well, indicating a neutralization of any negative charges through binding to curcumin (FIG. 13a). For Q, zeta potential in the absence of curcumin is 19.1±2.5 mV, with a steady increase up to a maximum value of 25.2±0.8 mV at a curcumin concentration of 40 μM (FIG. 13b). Above a molar concentration of 40 μM curcumin, however, zeta potential drops to values similar to Q in the absence of curcumin suggesting that neutralization is occurring by curcumin on the fiber surface. By contrast, L possesses a much lower zeta potential than Q both in the absence and presence of curcumin at all concentrations studied (FIG. 13a). Count rate from dynamic light scattering (DLS) is also studied to assess aggregation. For Q (in which the concentration was held constant at 10 μM), a steady increase in response to higher curcumin concentrations is observed (FIG. 13b), however count rate could not be obtained for L as the particles did not generate a high enough signal for detection, confirming the absence of aggregates. Absorbance of proteins at 420 nm in the presence of curcumin display a similar increasing trend (FIG. 13b, FIGS. 21a-21b). While the zeta potential, count rate, and absorbance data values for Q are similar to those exhibited by wt on a macromolecular level (FIGS. 21a-21b), analysis of Coulombic surface charge shows that on a molecular level the two protein assemblies have very different charge distributions. Our CD studies have confirmed that increasing molar ratios of curcumin affects only helical packing, not protein conformation.

Figure 22R:
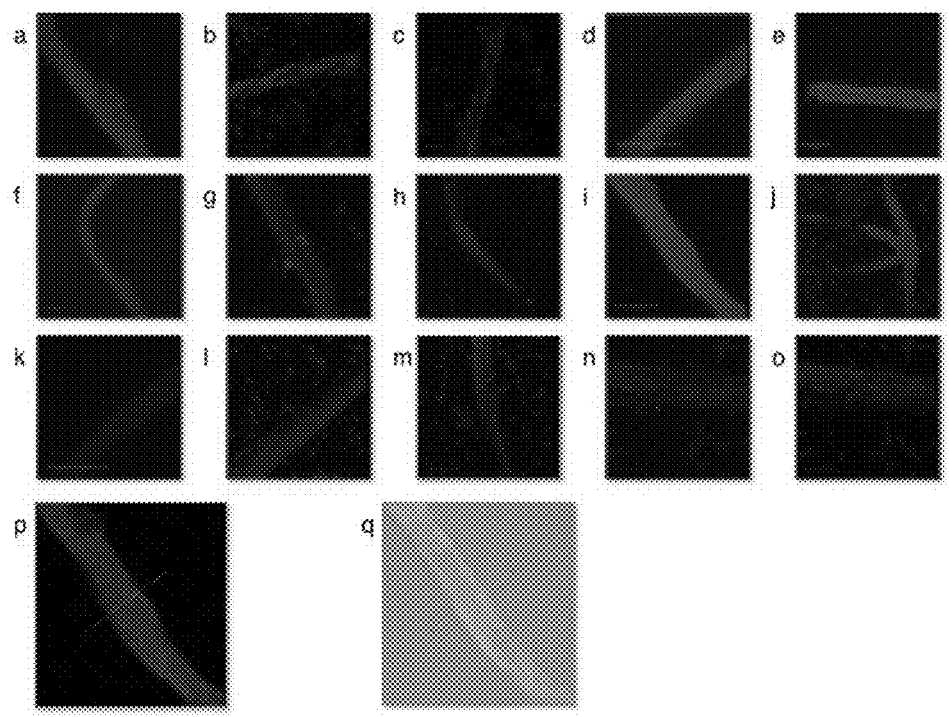
Figure 22R:
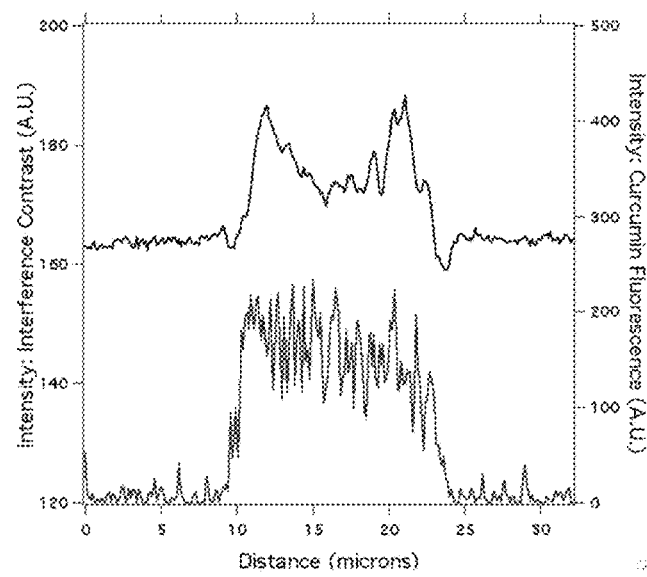

We have engineered proteins that can hierarchically assemble into mesofibers with the assistance of small molecules through encapsulation and aggregation (FIG. 22a-22q). We have demonstrated the synthesis of protein fibers of dimensions comparable to α-keratin, collagen, and spider silk with the added functionality of small molecule binding. These fibers are useful for tissue engineering and delivery of curcumin and other therapeutic small molecules.

Example 3

This example describes further characterization of the protein fibers of this disclosure. As discussed above, we observed that nanoscale Q fibers aggregate to form mesoscale protein fibers upon addition of curcumin. In addition, we examined the ability of C, Q, and wt COMPcc$^s$ to bind with two fatty acid chains: myristic acid and palmitic acid. Protein fibers formed in the presence of these fatty acids are shown in scanning electron micrographs in FIGS. 27a-27c and FIGS. 28a-28c. Samples were prepared by mixing fatty acid solution in a 1:1 molar ratio with COMP solution. The resulting solution was allowed to stand for 6 hours. Samples were prepared by depositing the fatty acid and COMP solution onto TEM grids that are supported on an SEM stub with carbon tape. The solution was allowed to dry, and was washed 3-5 times with water. The sample was allowed to dry between each wash. The images were taken on an SEM under high vacuum. Buffer conditions were pH 4 in 50 mM phosphate buffer.

Thus these proteins can be used as drug delivery vehicles, where cargo can be small, hydrophobic molecules. The binding of fatty acid chains also makes these protein materials interesting materials to stabilize fatty acids in the use of cosmeceuticals such as topical moisturizers, shampoos, soaps, etc. Some of the fatty acids that are widely used in the cosmeceutical industry include linoleic acid, gamma-linolenic acid, arachidonic acid, alpha-linolenic acid, and its longer chain derivatives eicosapentaenoic acid and docosahexaenoic acid.

Our nanofibers only require a single type of protein to form nanoscale materials that are loaded with small molecules, (2) our proteins form fibers as opposed to core-shell nanoparticles, and (3) combination of different (potentially more than two) therapeutic molecules can be accomplished by creating formulations of the same protein that has been separately loaded with the various small molecules and subsequently mixed.

Example 4

This example describes the binding of metal nanoparticles to the nanofibers of the present disclosure. As an example, metal nanoparticle temptation for materials synthesis under ambient conditions on the benchtop was carried out.

Specifically, pure, denatured protein which was dissolved in a buffer of 6 M urea was dialyzed into 2 L volumes of buffer successively halving the urea concentration: from 3 M to 1.5 M to 0.75 M followed by 3×2 L volumes of buffer containing 0 M urea. Dialysis was performed under conditions of constant mixing of the buffer and at 4° C. for a total of at least 36 h. Concentrations of phosphate buffer ranged from 10-50 mM, where fibers formed readily at 50 mM phosphate buffer but not below. pH 4, 8, and 10 were studied for fiber formation. Buffers were pH adjusted using concentrated volumes of HCl and/or NaOH. C and Q with incorporated trifluoroleucine and the wt equivalents was obtained with 100 and 500 mM in 50 mM phosphate buffer at pH 8. In addition, 5, 10, 20, and 40 v/v % trifluoroethanol (TFE) was added to buffer to study fiber formation as well, as this organic solvent is known to enhance α-helicity. AuNP-loaded protein films were formed by taking C or Q protein at 50 mM phosphate buffer pH 8 and templating $HAuCl_4$ from solution by reducing it with $NaBH_4$.

Figure 29:
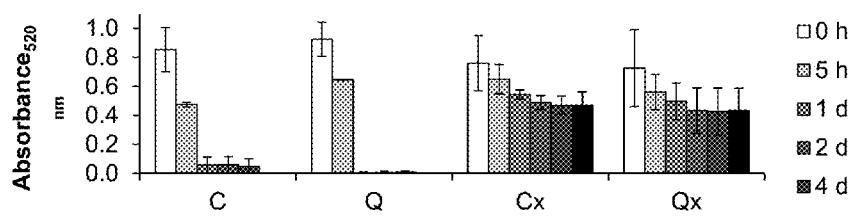
FIG. 29. Normalized absorbance of protein-AuNP complexes at 520 nm Error bars represent standard deviation of triplicate measurements for C, Cx, Q and Qx.
Figure 30:
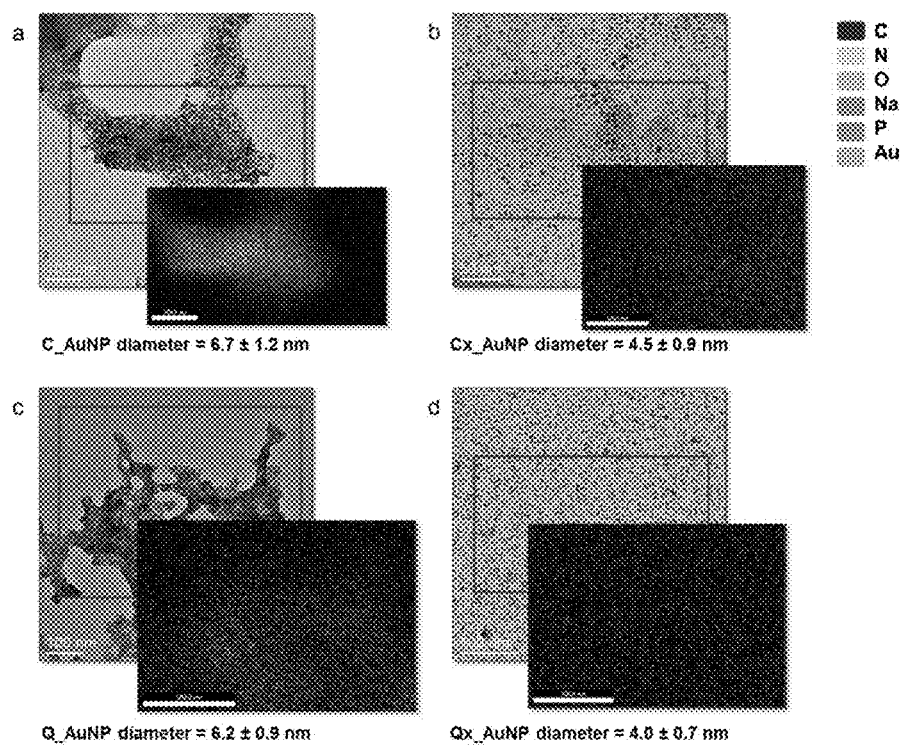
FIGS. 30a-30d. Transmission electron micrographs and elemental maps for C (a), Cx (b), Q (c), and Qx (d). Data acquired for each of the elemental maps resulted from the area outlined in red in the corresponding TEM image. Maps display location of signals resulting from C (purple), N (pink), oxygen (lime green), Na (rust), P (neon green), and Au (orange). Scale bars in TEM micrographs are 50 nm in (b) and 100 nm in (a), (c), and (d). Scale bars on EDAX maps are 100 nm in (a), (b), and (d) and 200 nm in (c).
Figure 31:
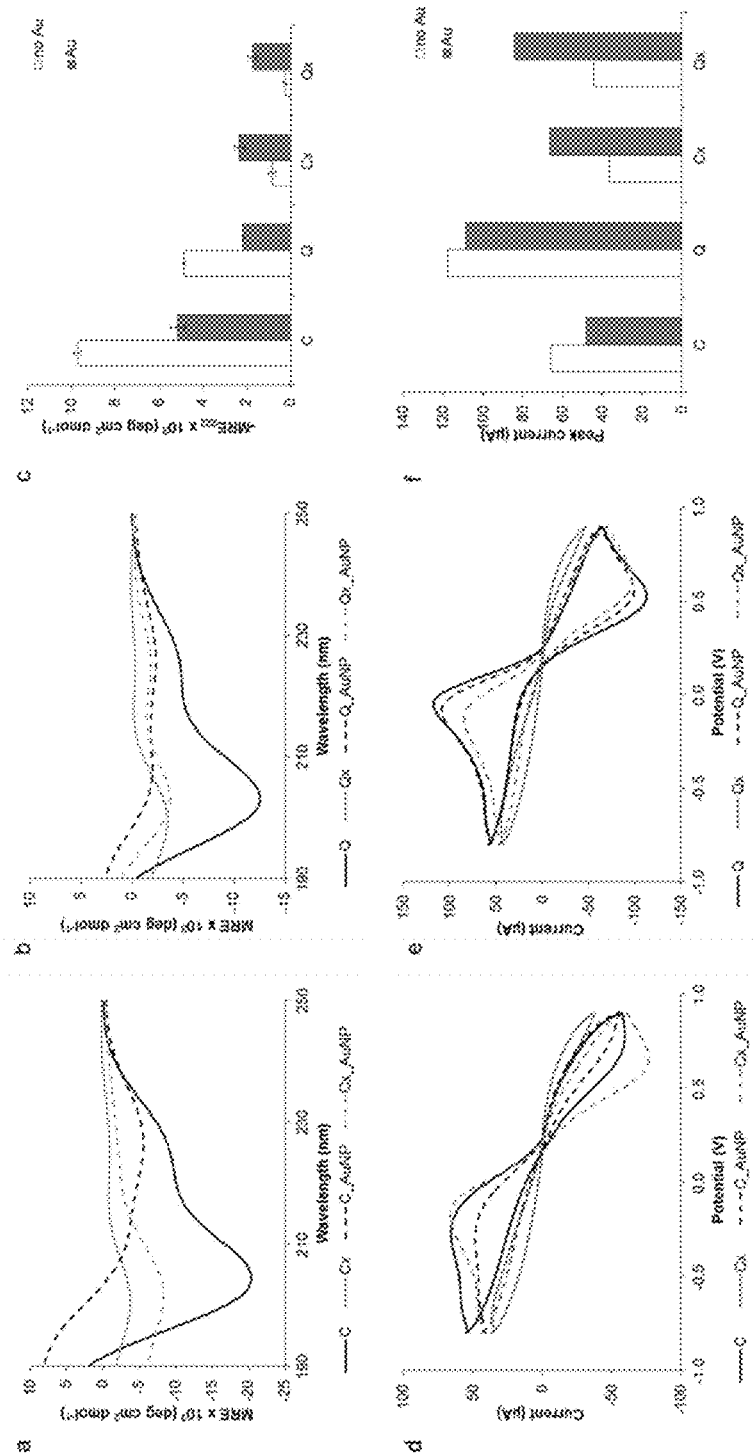
FIGS. 31a-31f. Wavelength scans of C, Cx, C in the presence of Au, and Cx in the presence of Au (a) and Q, Qx, Q in the presence of Au, and Qx in the presence of Au (b). CD data is averaged from three replicates. -MRE value at 222 nm for proteins in the absence of presence of Au (c). Error bars of $-MRE_{222}$ represent standard error from duplicate measurements. Cyclic voltammograms of 8 µM C, Cx, C_AuNP, and Cx_AuNP (d) and 8 µM Q, Qx, Q_AuNP, and Qx_AuNP (e) in the presence of 10 mM $K_4Fe(CN)_6.3H_2O$ and 10 mM $K_3Fe(CN)_6$. Cathodic peak currents of proteins in the absence and presence of Au are plotted in (f).
Figure 32:
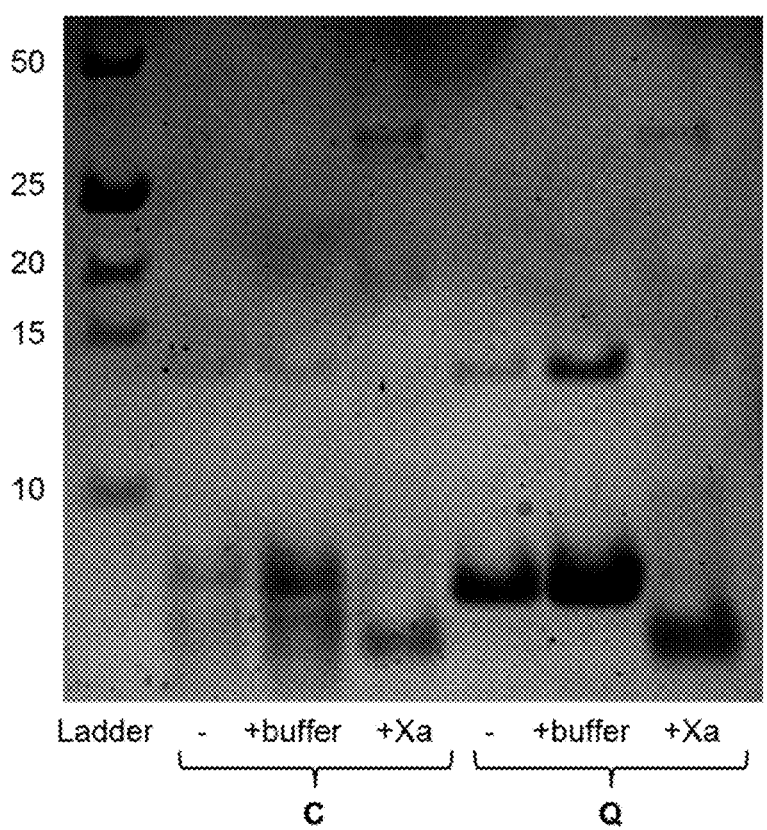
FIG. 32. SDS-PAGE gel showing cleavage of histidine tags for both C and Q. Lanes (from left to right) are ladder, C protein (6.31 kDa), C with cleavage buffer (6.31 kDa), C after incubation with Factor Xa (4.45 kDa), Q protein (6.31 kDa), Q with cleavage buffer (6.31 kDa), and Q after incubation with Factor Xa (4.45 kDa).
Figure 33:
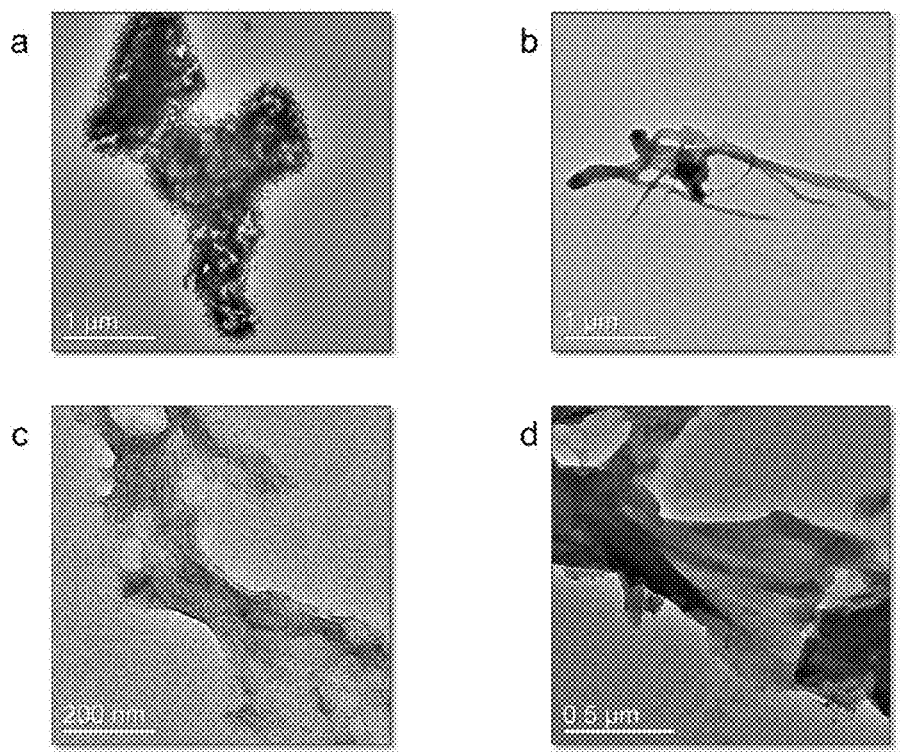
FIGS. 33a-33d. Transmission electron micrographs showing aggregates formed by C (a), fibers of Q (b), and sheet-like structures seen from cleaved proteins Cx (c) and Qx (d). Scale bars are 1 µm in (a) and (b), 200 nm in (c) and 0.5 µm in (d).
Figure 34:
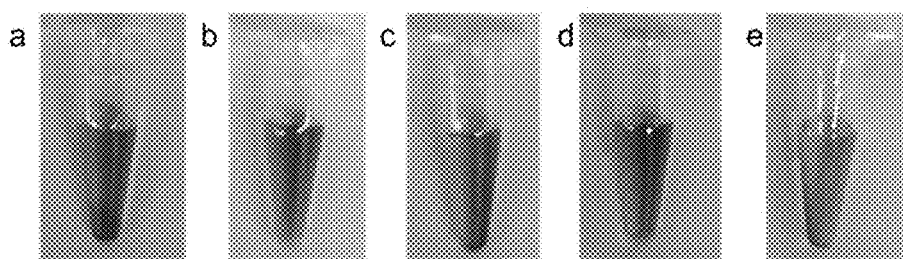
FIGS. 34a-34e. Photos of protein templated with AuNPs, taken immediately after templation. C (a) and Q (c) have a dark purple hue, similar to that seen in the absence of any protein (e). Cleaved proteins Cx (b) and Qx (d), on the other hand, have a pinkish hue that is maintained over a period of 8 days.
Figure 35:
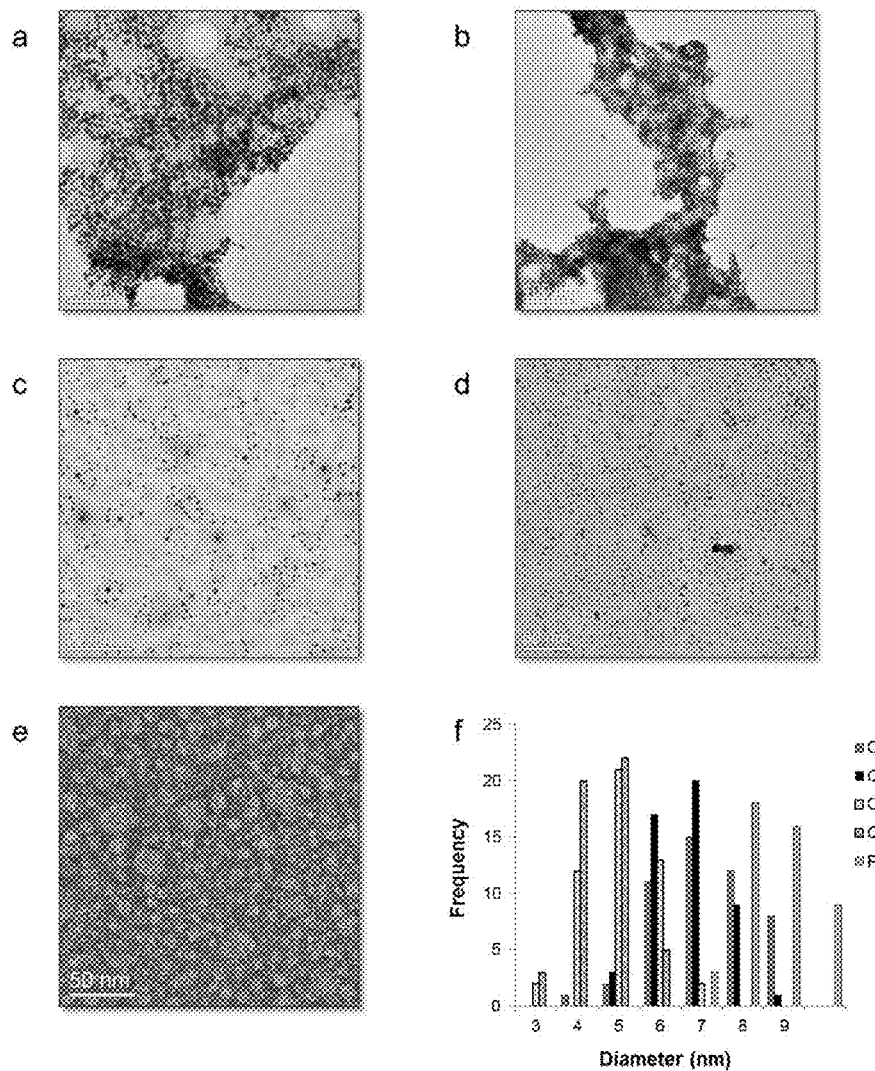
FIGS. 35a-35f. Transmission electron micrographs for C_AuNP (a), Q_AuNP (b), Cx_AuNP (c), Qx_AuNP (d), and AuNP in the absence of protein (in phosphate buffer) (e). Scale bars are 50 nm in (a), (c), (d), and (e) and 100 nm in (b). Histogram of nanoparticle sizes (f) shows that cleaved proteins template smaller AuNPs than his tagged proteins.
Figure 36:
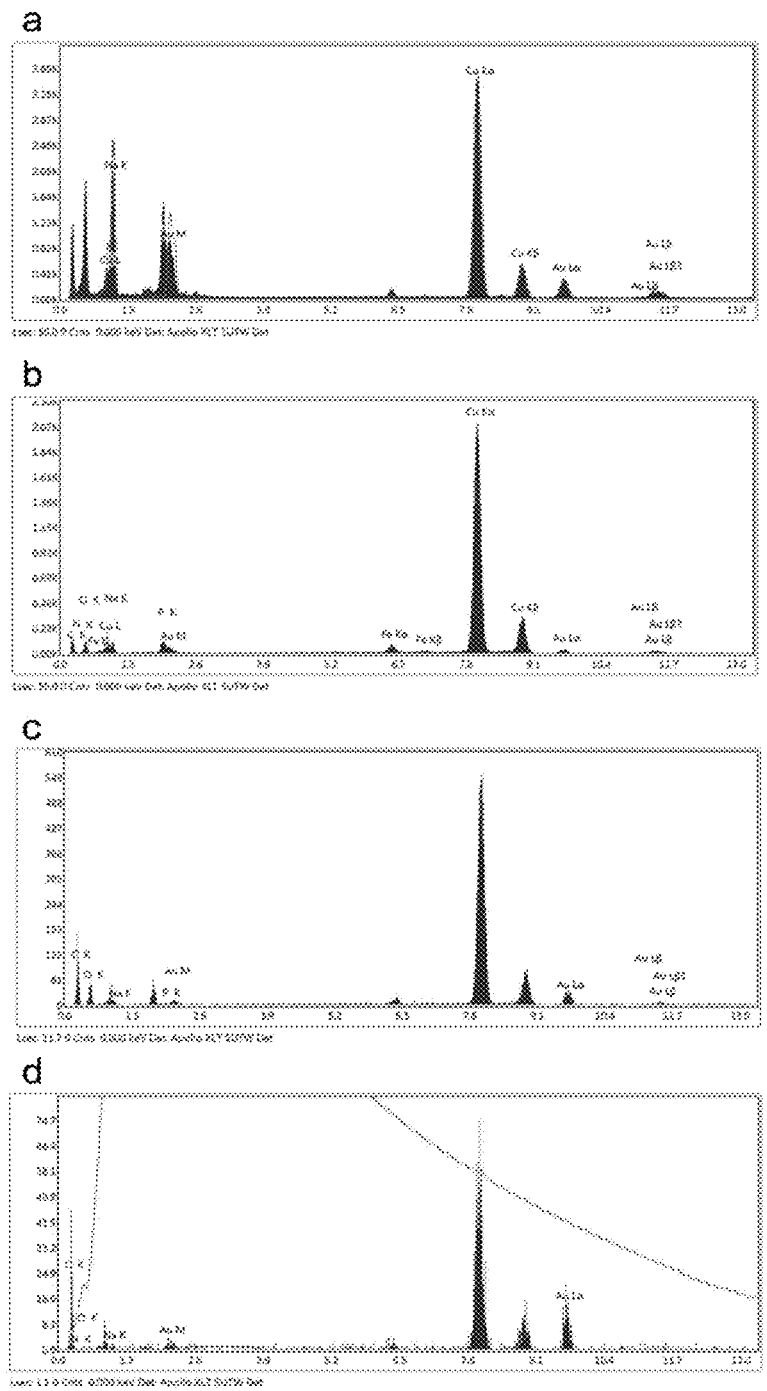
FIGS. 36a-36d. EDS spectra from C_AuNP (a), Q_AuNP (b), Cx_AuNP (c), and Qx_AuNP.
Figure 37:
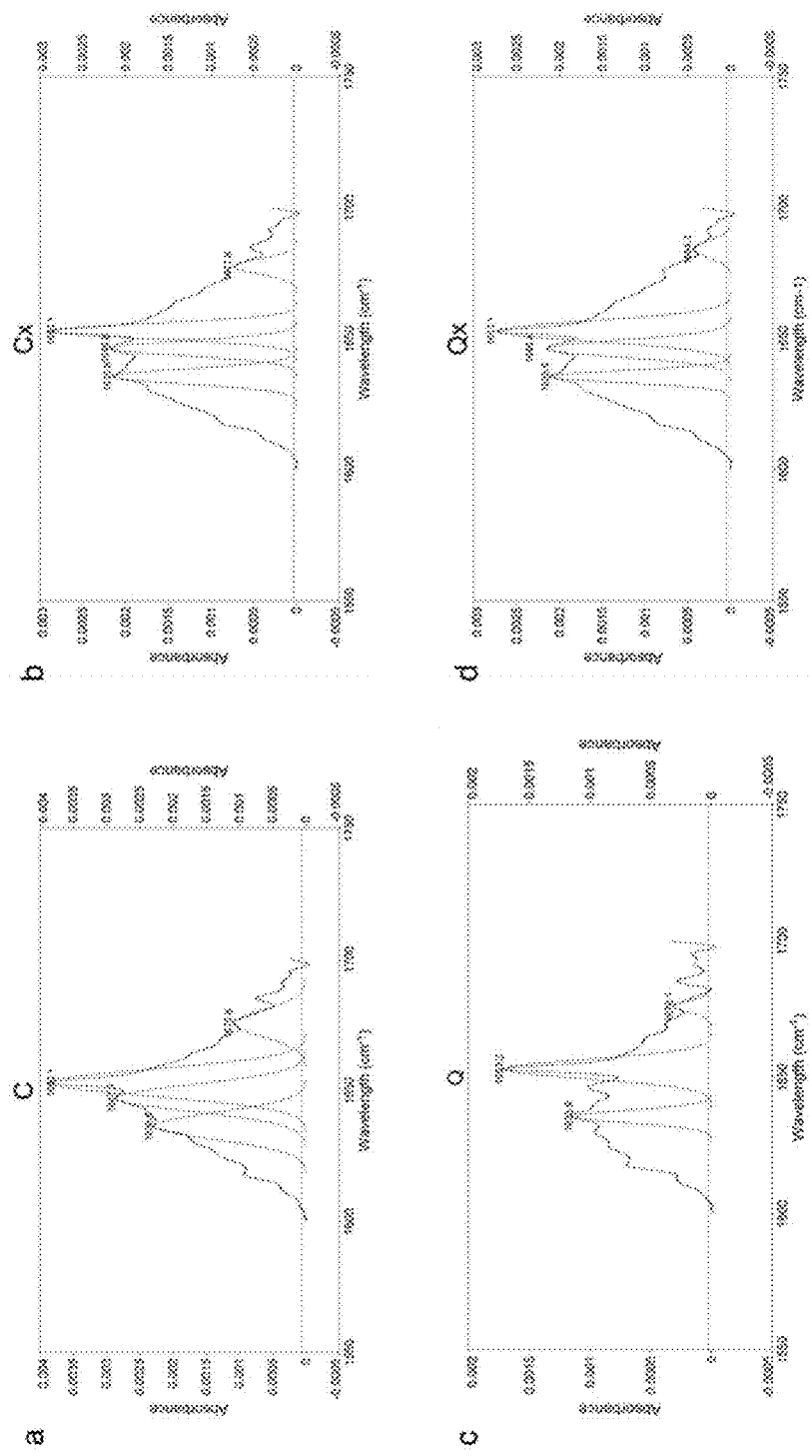
FIGS. 37a-37d. Fourier transform self-deconvoluted spectra of proteins in 50 mM PB 8: C (a), Cx (b), Q (c), Qx (d). Each spectrum represents the average of two trials.
Figure 38:
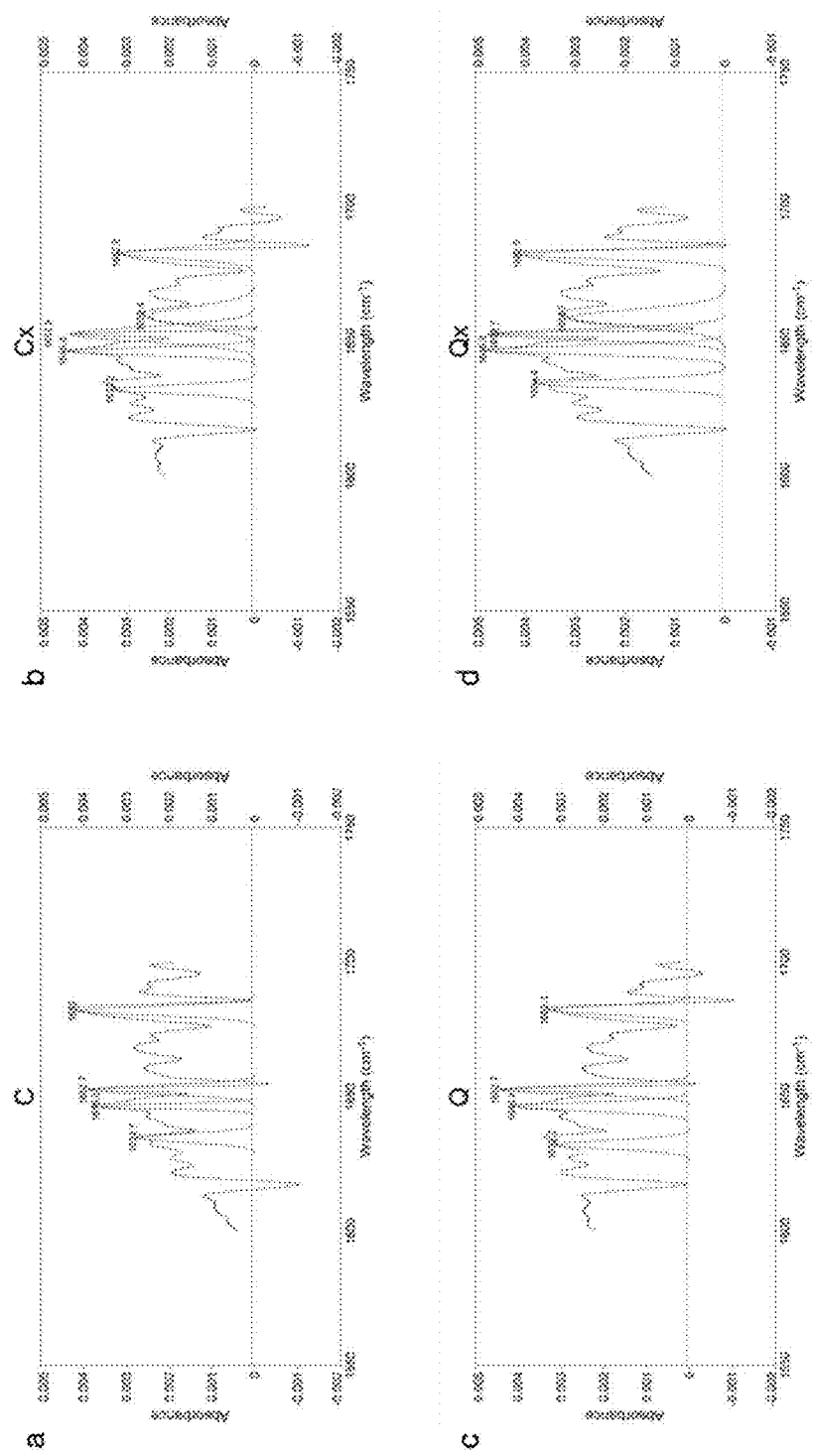
FIGS. 38a-38d. Fourier transform self-deconvoluted spectra of proteins after gold temptation in 50 mM PB 8: C (a), Cx (b), Q (c), Qx (d). Each spectrum represents the average of two trials.

Proteins C and Q were used to template gold nanoparticles in solution. These materials were found to aggregate rapidly, sequestering essentially all gold in the bulk volume. We show that C and Q proteins are capable of gold deposition onto glassy carbon electrode surfaces under ambient conditions (FIGS. 29, 30, 31). In addition, C and Q have been shown to be able to create monodisperse AuNP precipitates on a protein film (FIG. 35). In order to compare the effect of the presence/absence of the 6×histidine tag that is known to successfully template AuNPs, we also generated variants of C and Q that are void of a 6×his tag, dubbed Cx and Qx, respectively. The sequences for these four proteins are given in (Table 9). Interestingly, Cx and Qx are also able to form monodisperse AuNPs which remain stable in solution (but not deposit on a uniform protein film as the C and Q constructs). These related proteins may also find interesting applications in the stabilization of AuNPs.

TABLE 9

Sequence information for C, Q, Cx, and Qx, from N-terminus
C-terminus, with the histidine tags in hold.

| His tag | abcdefg | abcdefg | abcdefg | abcdefg | abcdefg | abcdefg | | |
|---|---|---|---|---|---|---|---|---|
| | 1 | 17 | 24 | 31 | 38 | 45 | 52 | |
| C | MRGSHHHHHHGSIEGR APQMLPE | LQETNAA | LQDVREL | LRQQVKE | ITFLKNT | SKL | | SEQ ID NO: 1 |
| | 1 | 17 | 20 | 27 | 34 | 41 | 48 | |
| Q | MRGSHHHHHHGSIEGR VKE | ITFLKNT | APQMLRE | LQETNAA | LQDVREL | LPQQSKL | | SEQ ID NO: 2 |
| | | 1 | 8 | 15 | 22 | 29 | 36 | |
| Cx | | APQMLRE | LQETNAA | LQDVREL | LRQQVKE | ITFLKNT | SKL | SEQ ID NO: 7 |
| | | 1 | 4 | 11 | 18 | 25 | 32 | |
| Qx | | VKE | ITFLKNT | APQMLRE | LQETNAA | LQDVREL | LRQQSKL | SEQ ID NO: 6 |

Secondary structure conformation based on ATR-FTIR data for 10 μM protein in 50 mM PB before and after templation of AuNPs is provided in Table 10. Percent composition was determined from relative areas of peaks fit to spectra (see spectra FIGS. 37a-37d, FIGS. 38a-38d).

TABLE 10

| Protein | | Conformation | | |
|---|---|---|---|---|
| | | α helix | β sheet | Random |
| C | — | — | 38 | 33 | 28 |
| | +AuNP | 30 | 54 | 16 |
| Q | — | — | 65 | 35 | 0 |
| | +AuNP | 30 | 43 | 27 |
| Cx | — | — | 37 | 36 | 27 |
| | +AuNP | 54 | 30 | 16 |
| Qx | — | — | 45 | 26 | 29 |
| | +AuNP | 48 | 32 | 20 |

Cleavage of his tags and TEM of aggregates formed by the sheet-like structures from the cleaved proteins is shown in FIG. 32 and FIGS. 33a-33d.

Figure 39:
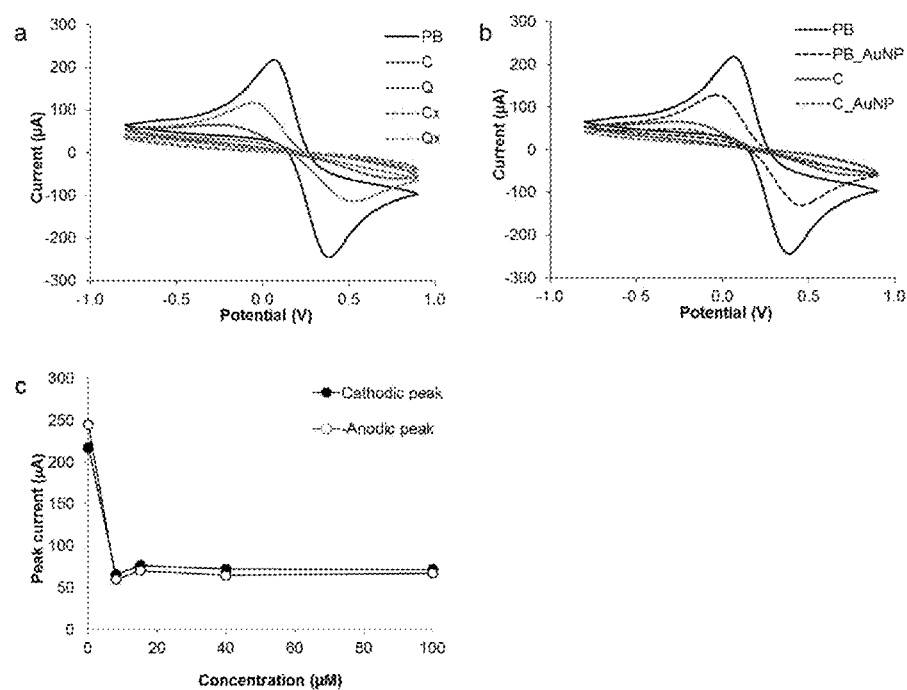
FIGS. 39a-39c. Cyclic voltammograms of PB (black), C (red), Q (blue), Cx (red dashed), and Qx (blue dashed) (a) and PB (black), PB_AuNP (black dashed), C (red), and C_AuNP (red dashed) (b) in the presence of 10 mM $K_4Fe(CN)_6.3H_2O$ and 10 mM $K_3Fe(CN)_6$. Cathodic and anodic peak currents of different concentrations of C in the absence of Au are plotted in (b).
Figure 40:
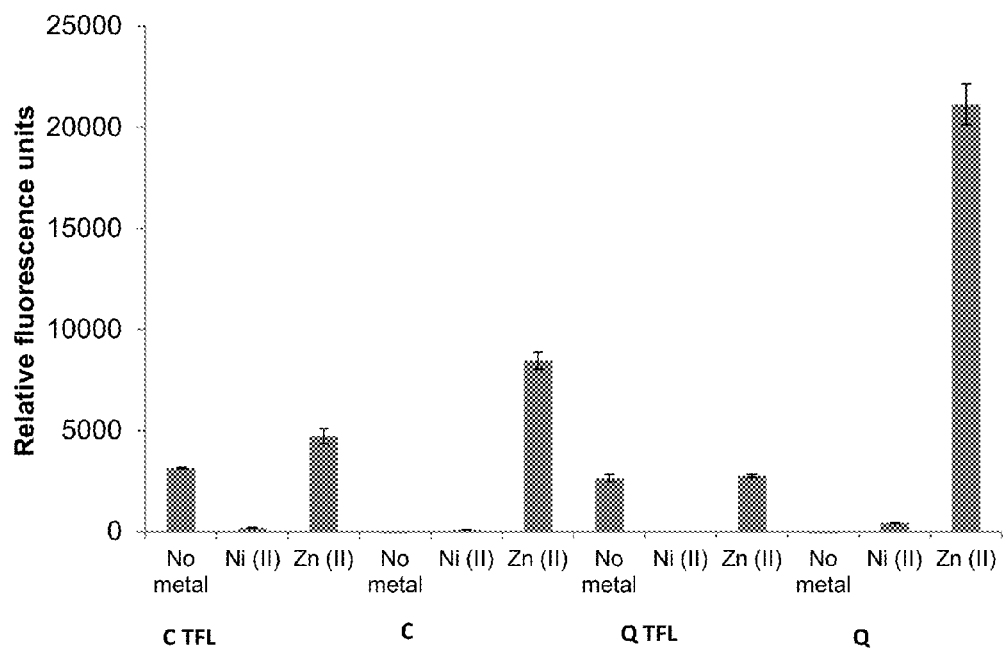
FIG. 40. Fluorescence of C and Q or with incorporated trifluoroleucine/TFL (C TFL and Q TFL) in the presence of no metal, Ni (II), or Zn (II) and curcumin. An increase in fluorescence indicates structural stability of the protein as it is able to bind with curcumin, the fluorescent probe in this case.

Photos of protein templated with AuNPs, taken immediately after templation. C (a) and Q (c) have a dark purple hue, similar to that seen in the absence of any protein (e). Cleaved proteins Cx (b) and Qx (d), on the other hand, have a pinkish hue that is maintained over a period of 8 days. EDS spectra from C_AuNP (a), Q_AuNP (b), Cx_AuNP (c), and Qx_AuNP (d). In the case of the cleaved proteins EDAX was used to confirm that protein was indeed surrounding the NPs. X-ray signals of elements corresponding to protein is seen throughout the elemental maps of cleaved proteins, confirming that protein material indeed surrounds the NPs, solvating them and enabling them to maintain their solubility over time. Increased count rates of Au X-ray signals from C and Q samples are observed compared with Cx and Qx, resulting from the high density of AuNPs in the aggregates formed by 6-His proteins. Structural changes of proteins due to soluble metal binding is provided. We carried out experiments on proteins related to C and Q that demonstrate the ability of metal nanoparticles to alter the secondary structure of these proteins. We introduced the incorporation of unnatural amino acid, trifluoroleucine (TFL) via residue-specific incorporation to produce fluorinated proteins, C TFL and Q TFL using a standard leucine auxotroph strain. Our data demonstrate that in the presence of $Zn^{2+}$, we can substantially increase the binding to small molecule for C and Q (FIGS. 39a-39c). This is presumably due to stabilization of helical conformation in the presence of $Zn^{2+}$ as demonstrated by FIG. 40. While the fluorinated C TFL and Q TFL protein maintain the small molecule binding in the presence of $Zn^{2+}$ and release the small molecule in the presence of $Ni^{2+}$ (FIGS. 39a-39c). These properties can be used to enhance binding or trigger the release of small molecules for applications in tissue engineering scaffolds and/or drug delivery.

Figure 41:
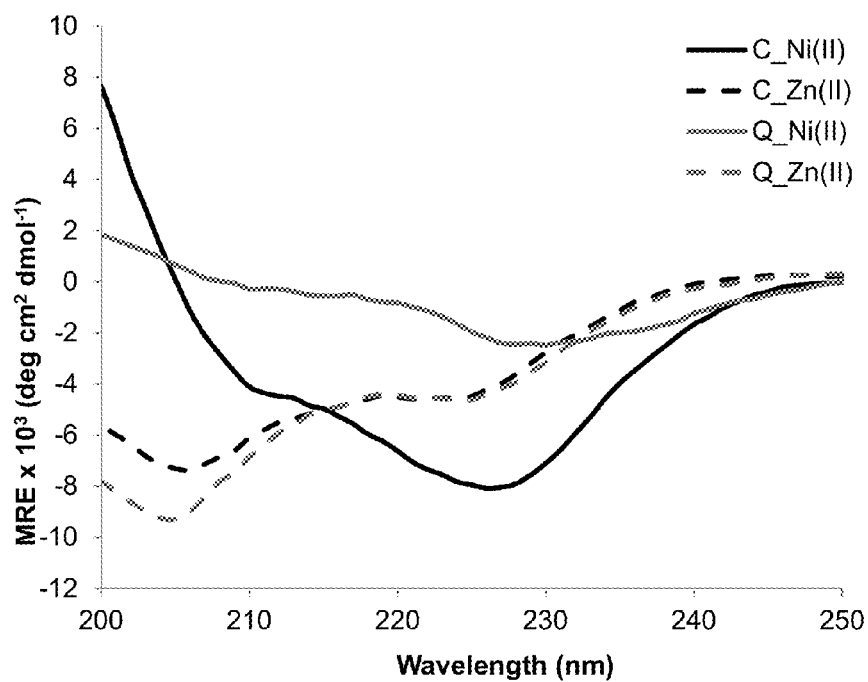
FIG. 41. Wavelength scans of C and Q in the presence of Ni (II) or Zn (II).

In the presence of $Zn^{2+}$, the proteins exhibit helical character, however, in the presence of $Ni^{2+}$, the scans indicate aggregation (FIG. 41)

The present proteins do not go from one structured state to another, but rather an unstructured state to a structured state, or vice versa (depending on the identity of the peptide and metal). Additionally, there are no bonds that form in response to the metals. This enables our assemblies to transition between structured and unstructured states reversibly. Our constructs can in the presence of the soluble metals enhance binding to small molecule or release it. Further, the metal binding of as we have observed can cause encapsulation or release of the small molecule dependent upon the construct and metal.

Example 5

Figure 42:
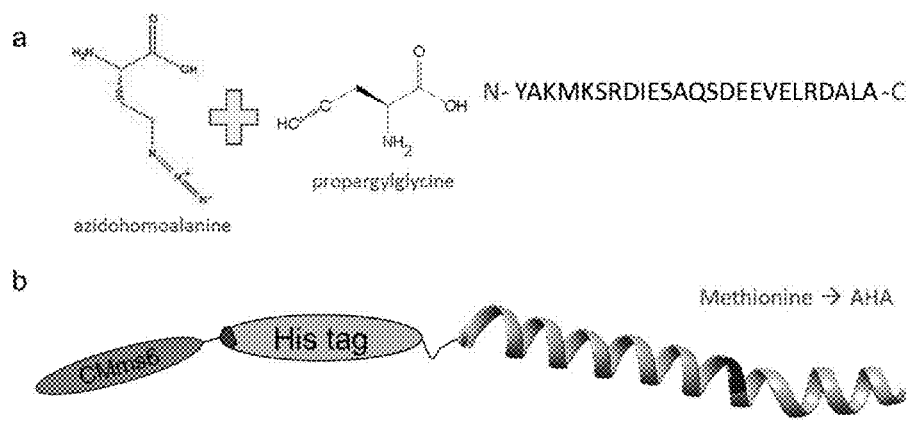
FIGS. 42a-42b. Schematic of click chemistry reaction that will enable functionalization of C and Q proteins with an orthogonal magnetite binding peptide, CMms6 (SEQ ID NO: 16), whose sequence is shown in (a). Azidohomoalanine (AHA) will be incorporated into C and Q in the place of methionine, which will react with CMms6 bearing an N-terminal propargylglycine via a Cu catalyzed click chemistry reaction (a). It is expected that CMms6 will be clicked on to the AHA at the N terminus of the proteins, as it is more solvent accessible (b).

This example describes the incorporation of an unnatural amino acid into the proteins. In this example, the unnatural amino acid azidohomoalanine (AHA) was used. The AHA bears an azido group which allows us to perform click-chemistry to attach any desired peptide ligand onto the protein fibers. In the case of AHA, the residue that we substituted out is methionine. This can be used to covalently attach an orthogonal peptide, which contains a peptide sequence capable of magnetite temptation. A schematic of the click chemistry is provided in FIGS. 42a-42b. Those skilled in the art will recognize that any position can be mutated.

An unnatural amino acid, azidohomoalanine, in the place of methionine using methionine auxotrophic (M15MA) cells was carried out. A magnetite binding peptide, CMms6 bearing an alkyne, (SEQ ID NO:16) was covalently attached via Cu-catalyzed click chemistry. The positive controls capable of magnetic nanoparticle templation were AHA+ CMms6. The negative control—incapable of magnetic nanoparticle templation were no AHA or CMms6

Figure 43:
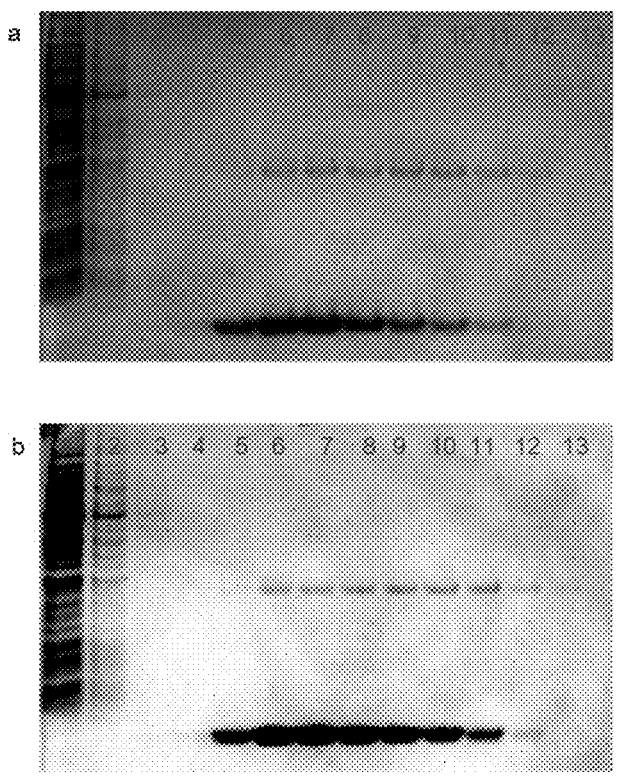
FIGS. 43a-43b. SDS-PAGE gels of purification of AHA-incorporated C (a) and Q (b), referred to as CAHA and QAHA. Lanes are as follows: 1 Supernatant after Ni-NTA binding, 2 Flow through, 3 and 4 20 mM imidazole, 5 100 mM imidazole, 6 and 7 200 mM imidazole, 8, 9, 10 500 mM imidazole, 11, 12, 13 1 M imidazole. Protein from lanes 5-10 of (a) and lanes 5-11 of (b) was dialyzed. Expected molecular weight of CAHA and QAHA is ~6.30 kDa. An oligomer of CAHA and QAHA was confirmed as the upper band in each gel.

AHA incorporated C and Q was purified by SDS PAGE (FIGS. 43a-43b). Results confirm the formation of an oligomer of CAHA and QAHA seen as the upper band in each gel.

Figure 44:
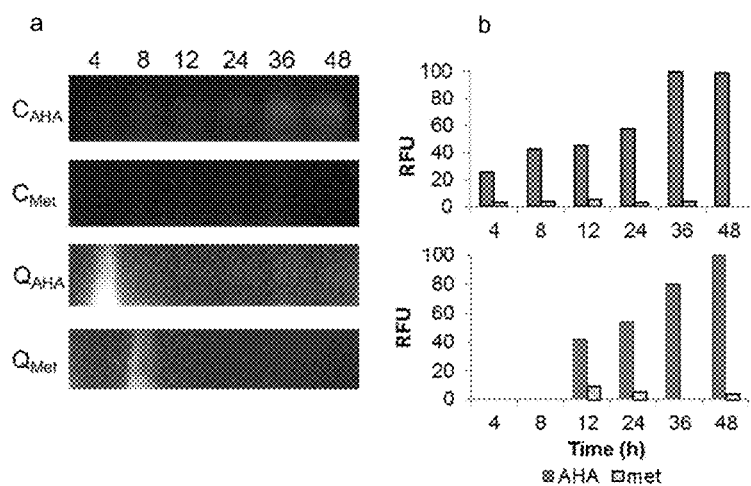
FIGS. 44a-44b. Click chemistry was performed on whole cell lysate containing expressed CAHA, Cmet (expressed with the natural set of 20 amino acids), QAHA, and Qmet. Fluorophore Chromeo494 bearing an alkyne group was clicked on to protein containing AHA, and in-gel fluorescence was used to evaluate fluorescence of chemically linked Chromeo494 over 48 h (a). The reaction was allowed to proceed for 48 h, taking aliquots at various time points to study reaction progress. As can be seen in the images of the lysate run on the gel (a), only CAHA and QAHA display any fluorescence. Quantitative analysis of the in-gel fluorescence was conducted and RFU was plotted for each sample in the column graphs. CAHA and Cmet are compared in (b), where grey columns represent CAHA and white columns Cmet. QAHA and Qmet are compared in (c), where grey columns represent QAHA and white columns Qmet. It is apparent that fluorescence values plateau after 48 h in the case of CAHA and reach maximum values for QAHA after 48 h as well. There is negligible fluorescence in methionine versions of C and Q.

Click chemistry was performed on whole cell lysate containing expressed CAHA, Cmet (expressed with the natural set of 20 amino acids), (FIGS. 44a-44b) QAHA, and Qmet. Fluorophore Chromeo494 bearing an alkyne group was clicked on to protein containing AHA, and in-gel fluorescence was used to evaluate fluorescence of chemically linked Chromeo494 over 48 h (a). The reaction was allowed to proceed for 48 h, taking aliquots at various time points to study reaction progress. As can be seen in the images of the lysate run on the gel (a), only CAHA and QAHA display any fluorescence. Quantitative analysis of the in-gel fluorescence was conducted and RFU was plotted for each sample in the column graphs. CAHA and Cmet are compared in (b), where grey columns represent CAHA and white columns Cmet. QAHA and Qmet are compared in (c), where grey columns represent QAHA and white columns Qmet. It is apparent that fluorescence values plateau after 48 h in the case of CAHA and reach maximum values for QAHA after 48 h as well. There is negligible fluorescence in methionine versions of C and Q.

Figure 45:
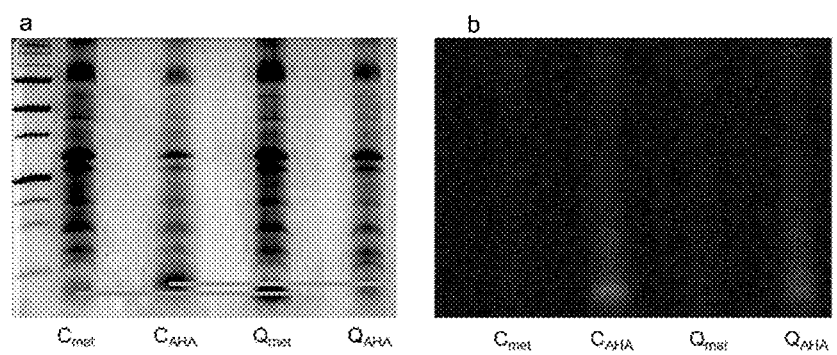
FIGS. 45a-45b. SDS-Page gels of click chemistry on whole cell lysate containing expressed CAHA, Cmet, QAHA, and Qmet after 48 h of incubation at 50° C. Coomassie-stained gel (a) shows a molecular weight shift in azidohomoalanine-containing variants that have been clicked with Chromeo494. Using the ladder as a standard, the shift was quantified as 1 kDa, corresponding well to 2×MWChromeo494 (1.1 kDa), indicating that close to two Chromeo494 molecules have been successfully clicked onto the AHA variants. The same gel visualized with a fluorescence filter (b) demonstrates that only CAHA Chromeo494 and QAHAChromeo494 display any fluorescence.

SDS-Page gels of click chemistry on whole cell lysate containing expressed CAHA, Cmet, QAHA, and Qmet after 48 h of incubation at 50° C. (FIGS. 45a-45b). Coomassie-stained gel (a) shows a molecular weight shift in azidohomoalanine-containing variants that have been clicked with Chromeo494. Using the ladder as a standard, the shift was quantified as 1 kDa, corresponding well to 2×MWChromeo494 (1.1 kDa), indicating that close to two Chromeo494 molecules have been successfully clicked onto the AHA variants. The same gel visualized with a fluorescence filter (b) demonstrates that only CAHA Chromeo494 and QAHAChromeo494 display any fluorescence.

Figure 46:
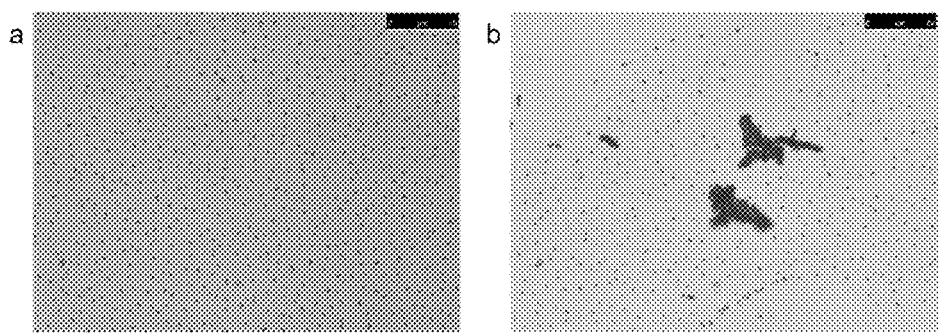
FIGS. 46a-46b. Phase contrast micrographs of magnetite nanoparticles formed by addition of ionic ferric/ferrous salts ($FeCl_3$+$FeSO_4$) and reduction by NaOH in the absence (a) and presence (b) of protein (Q).

Phase contrast micrographs of magnetite nanoparticles formed by addition of ionic ferric/ferrous salts ($FeCl_3$+$FeSO_4$) and reduction by NaOH in the absence (a) and presence (b) of protein (Q) are shown in FIGS. 46a-46b. These results indicate that these nanofibers can be used to generate monodisperse, stable magnetic nanoparticles. Potential applications are for materials in biomedical imaging or directing drug delivery via external methods, such as via application of magnetic fields. Biosensing applications are also envisioned, as structural changes in the protein can affect nanoparticle temptation, and vice versa.

Although the present invention has been described with respect to one or more particular embodiments, it will be understood that other embodiments of the present invention may be made without departing from the spirit and scope of the present invention and such embodiments are intended to be within the scope of this disclosure.

---

SEQUENCE LISTING:

CC protein
(SEQ ID NO: 1)
MRGSHHHHHHGSIEGRAPQMLRELQETNAALQDVRELLRQQVKEITFLKN
TSKL Q54 protein
(SEQ ID NO: 2)
MRGSHHHHHHGSIEGRVKEITFLKNTAPQMLRELQETNAALQDVRELLRQ
QSKL L44 protein
(SEQ ID NO: 3)
MRGSHHHHHHGSIEGRLQDVERLLRQQVKEITFLKNTAPQMLRELQETNA
ASKL COMPcc protein
(SEQ ID NO: 4)
MRGSHHHHHHGSGDLAPQMLRELQETNAALQDVRELLRQQVKEITFLKNT
VMESDASGKLN COMPcc$^S$ gene sequence
(SEQ ID NO: 5)
TCA ATT GTG AGC GGA TAA CAA TTT CAC ACA GAA TTC
ATT AAA GAG GAG AAA TTA ACT ATG AGA GGA TCG CAT

---

SEQUENCE LISTING:

CAC CAT CAC CAT CAC GGA TCC GGT GAC CTG GCG CCG
CAG ATG CTG CGT GAA CTG CAG GAA ACC AAC GCG GCG
CTG CAG GAC GTT CGT GAA CTG CTG CGT CAG CAG GTT
AAA GAA ATC ACC TTC CTG AAA AAC ACC GTT ATG GAA
TCT GAC GCG TCT GGT AAG CTT AAT TAG CTG AGC TTG
GAC TCC TGT TGA TAG ATC CAG TAA TGA CCT CAG AAC
TCC ATC TGG ATT.

Qx protein
(SEQ ID NO: 6)
VKEITFLKNTAPQMLRELQETNAALQDVRELLRQQSKL

Cx protein
(SEQ ID NO: 7)
APQMLRELQETNAALQDVRELLRQQVKEITFLKNTSKL

Primer L Fwd1
(SEQ ID NO: 8)
GCATGGGATCCATCGAAGGTCGCCTGCAGGACGTTCGTGAAC

Primer L Rev1
(SEQ ID NO: 9)
CATCTGCGGCGCGGTGTTTTTCAGGAAGG

Primer L Fwd2
(SEQ ID NO: 10)
GCCGCAGATGCTGCGT

Primer L Rev2
(SEQ ID NO: 11)
GCATGAAGCTTTGACGCCGCGTTGGTTTCCTG

Primer Q Fwd1
(SEQ ID NO: 12)
GCATGGGATCCATCGAAGGTCGCGTTAAAGAAATCACCTTC

Primer Q Rev2
(SEQ ID NO: 13)
GCATGAAGCTTTGACTGCTGACGCAGCAGTTC

DNA Sequence for L
(SEQ ID NO: 14)
GGATCCATCGAAGGTCGCCTGCAGGACGTTCGTGAACTGCTGCGTCAGC
AGGTTAAAGAAATCACCTTCCTGAAAAACACCGCGCCGCAGATGCTGCG
TGAACTGCAGGAAACCAACAATCAAAGCTT DNA Sequence for Q
(SEQ ID NO: 15)
GGATCCATCGAAGGTCGCGTTAAAGAAATCACCTTCCTGAAAAACACCG
CGCCGCAGATGCTGCGTGAACTGCAGGAAACCAACGCGGCGCTGCAGGA
CGTTCGTGAACTGCTGCGTCAGCAGTCAAAGCTT Magnetite binding peptide, CMms6
(SEQ ID NO: 16)
YAKMKSRDIESAQSDEEVELRDALA

We claim:

1. A protein nanofiber comprising a plurality of fibrils, each fibril being formed by coiled-coil homopentamers of a protein, wherein the protein has a sequence of SEQ ID NO. 1 or SEQ ID NO. 2.

2. The protein nanofiber of claim 1, wherein the plurality of fibrils associate with each other along the longitudinal axis to form the nanofibers.

3. The protein nanofiber of claim 2, wherein the diameter of the nanofibers is from 20 nm to 1 micron.

4. The protein nanofiber of claim 3, wherein the diameter of the nanofibers is from 50 to 200 nm.

5. The protein nanofiber of claim 2, wherein the diameter of the fibril is from 1-10 nm.

6. The protein nanofiber of claim 2, wherein the length of the nanofibers is from 1 micron to 30 microns.

7. The protein nanofiber of claim 1, which has associated thereon a plurality of non-protein hydrophobic molecules.

8. A composition comprising the protein nanofibers of claim 1 in a suitable buffer.

9. The composition of claim 8, wherein the protein nanofibers have non-protein hydrophobic molecules bound thereto.

10. The composition of claim 9, wherein the suitable buffer is a phosphate buffer.

11. The composition of claim 10, wherein the pH of the buffer is from 4 to 8.

12. A method of making the nanofibers of claim 1, comprising mixing a plurality of proteins of SEQ ID NO:1 or SEQ ID NO:2 under conditions that permit self-assembly of the proteins to form homopentamers thereby allowing the formation of fibrils, and nanofibers.

13. The method of claim 10, further comprising contacting the nanofibers with a metal nanoparticle precursor such that a film comprising the protein of the nanofibers having metal nanoparticles disposed therein is formed.

14. A protein nanofiber comprising a plurality of fibrils, each fibril being formed by coiled-coil homopentamers of a protein, wherein the protein has a sequence of SEQ ID NO:1 or SEQ ID NO:2, in which a methionine in the protein of SEQ ID NO:1 or SEQ ID NO:2 is replaced with azidohomoalanine (AHA), the protein is conjugated to a magnetite binding peptide of SEQ ID NO:16, and the conjugate is incorporated into magnetic nanoparticles.

* * * * *

SEQUENCE LISTING

<160> NUMBER OF SEQ ID NOS: 16

<210> SEQ ID NO 1
<211> LENGTH: 54
<212> TYPE: PRT
<213> ORGANISM: artificial sequence
<220> FEATURE:
<223> OTHER INFORMATION: synthetic protein

<400> SEQUENCE: 1

Met Arg Gly Ser His His His His His His Gly Ser Ile Glu Gly Arg
1               5                   10                  15

Ala Pro Gln Met Leu Arg Glu Leu Gln Glu Thr Asn Ala Ala Leu Gln
            20                  25                  30

Asp Val Arg Glu Leu Leu Arg Gln Gln Val Lys Glu Ile Thr Phe Leu
        35                  40                  45

Lys Asn Thr Ser Lys Leu
        50

<210> SEQ ID NO 2
<211> LENGTH: 54
<212> TYPE: PRT
<213> ORGANISM: artificial sequence
<220> FEATURE:
<223> OTHER INFORMATION: synthetic protein

<400> SEQUENCE: 2

Met Arg Gly Ser His His His His His His Gly Ser Ile Glu Gly Arg
1               5                   10                  15

Val Lys Glu Ile Thr Phe Leu Lys Asn Thr Ala Pro Gln Met Leu Arg
            20                  25                  30

Glu Leu Gln Glu Thr Asn Ala Ala Leu Gln Asp Val Arg Glu Leu Leu
        35                  40                  45

Arg Gln Gln Ser Lys Leu
        50

<210> SEQ ID NO 3
<211> LENGTH: 54
<212> TYPE: PRT
<213> ORGANISM: artificial sequence
<220> FEATURE:
<223> OTHER INFORMATION: synthetic protein

<400> SEQUENCE: 3

Met Arg Gly Ser His His His His His His Gly Ser Ile Glu Gly Arg
1               5                   10                  15

Leu Gln Asp Val Glu Arg Leu Leu Arg Gln Gln Val Lys Glu Ile Thr
            20                  25                  30

Phe Leu Lys Asn Thr Ala Pro Gln Met Leu Arg Glu Leu Gln Glu Thr
        35                  40                  45

Asn Ala Ala Ser Lys Leu
        50

<210> SEQ ID NO 4
<211> LENGTH: 61
<212> TYPE: PRT
<213> ORGANISM: human

<400> SEQUENCE: 4

Met Arg Gly Ser His His His His His His Gly Ser Gly Asp Leu Ala
1               5                   10                  15

Pro Gln Met Leu Arg Glu Leu Gln Glu Thr Asn Ala Ala Leu Gln Asp
            20                  25                  30

Val Arg Glu Leu Leu Arg Gln Gln Val Lys Glu Ile Thr Phe Leu Lys
        35                  40                  45

Asn Thr Val Met Glu Ser Asp Ala Ser Gly Lys Leu Asn
    50                  55                  60

<210> SEQ ID NO 5
<211> LENGTH: 300
<212> TYPE: DNA
<213> ORGANISM: human

<400> SEQUENCE: 5
tcaattgtga gcggataaca atttcacaca gaattcatta agaggagaaa attaactatg      60
agaggatcgc atcaccatca ccatcacgga tccggtgacc tggcgccgca gatgctgcgt     120
gaactgcagg aaaccaacgc ggcgctgcag gacgttcgtg aactgctgcg tcagcaggtt     180
aaagaaatca ccttcctgaa aaacaccgtt atggaatctg acgcgtctgg taagcttaat     240
tagctgagct tggactcctg ttgatagatc cagtaatgac ctcagaactc catctggatt     300

<210> SEQ ID NO 6
<211> LENGTH: 38
<212> TYPE: PRT
<213> ORGANISM: artificial sequence
<220> FEATURE:
<223> OTHER INFORMATION: synthetic protein

<400> SEQUENCE: 6

Val Lys Glu Ile Thr Phe Leu Lys Asn Thr Ala Pro Gln Met Leu Arg
1               5                   10                  15

Glu Leu Gln Glu Thr Asn Ala Ala Leu Gln Asp Val Arg Glu Leu Leu
            20                  25                  30

Arg Gln Gln Ser Lys Leu
        35

<210> SEQ ID NO 7
<211> LENGTH: 38
<212> TYPE: PRT
<213> ORGANISM: artificial sequence
<220> FEATURE:
<223> OTHER INFORMATION: synthetic protein

<400> SEQUENCE: 7

Ala Pro Gln Met Leu Arg Glu Leu Gln Glu Thr Asn Ala Ala Leu Gln
1               5                   10                  15

Asp Val Arg Glu Leu Leu Arg Gln Gln Val Lys Glu Ile Thr Phe Leu
            20                  25                  30

Lys Asn Thr Ser Lys Leu
        35

<210> SEQ ID NO 8
<211> LENGTH: 42
<212> TYPE: DNA
<213> ORGANISM: artificial sequence
<220> FEATURE:
<223> OTHER INFORMATION: primer

<400> SEQUENCE: 8
gcatgggatc catcgaaggt cgcctgcagg acgttcgtga ac                         42

<210> SEQ ID NO 9

```
<211> LENGTH: 29
<212> TYPE: DNA
<213> ORGANISM: artificial sequence
<220> FEATURE:
<223> OTHER INFORMATION: primer

<400> SEQUENCE: 9
catctgcggc gcggtgtttt tcaggaagg                              29

<210> SEQ ID NO 10
<211> LENGTH: 30
<212> TYPE: DNA
<213> ORGANISM: artificial sequence
<220> FEATURE:
<223> OTHER INFORMATION: primer

<400> SEQUENCE: 10
ctgaaaaaca ccgcgccgca gatgctgcgt                             30

<210> SEQ ID NO 11
<211> LENGTH: 32
<212> TYPE: DNA
<213> ORGANISM: artificial sequence
<220> FEATURE:
<223> OTHER INFORMATION: primer

<400> SEQUENCE: 11
gcatgaagct tgacgccgc gttggtttcc tg                           32

<210> SEQ ID NO 12
<211> LENGTH: 41
<212> TYPE: DNA
<213> ORGANISM: artificial sequence
<220> FEATURE:
<223> OTHER INFORMATION: primer

<400> SEQUENCE: 12
gcatgggatc catcgaaggt cgcgttaaag aaatcacctt c                41

<210> SEQ ID NO 13
<211> LENGTH: 32
<212> TYPE: DNA
<213> ORGANISM: artificial sequence
<220> FEATURE:
<223> OTHER INFORMATION: primer

<400> SEQUENCE: 13
gcatgaagct tgactgctg acgcagcagt tc                           32

<210> SEQ ID NO 14
<211> LENGTH: 128
<212> TYPE: DNA
<213> ORGANISM: artificial sequence
<220> FEATURE:
<223> OTHER INFORMATION: DNA coding for L

<400> SEQUENCE: 14
ggatccatcg aaggtcgcct gcaggacgtt cgtgaactgc tgcgtcagca ggttaaagaa    60
atcaccttcc tgaaaaacac cgcgccgcag atgctgcgtg aactgcagga aaccaacaat   120
caaagctt                                                           128

<210> SEQ ID NO 15
<211> LENGTH: 132
<212> TYPE: DNA
<213> ORGANISM: artificial sequence
```

```
<220> FEATURE:
<223> OTHER INFORMATION: DNA sequence encoding Q

<400> SEQUENCE: 15
ggatccatcg aaggtcgcgt taaagaaatc accttcctga aaaacaccgc gccgcagatg      60
ctgcgtgaac tgcaggaaac caacgcggcg ctgcaggacg ttcgtgaact gctgcgtcag     120
cagtcaaagc tt                                                         132

<210> SEQ ID NO 16
<211> LENGTH: 25
<212> TYPE: PRT
<213> ORGANISM: artificial sequence
<220> FEATURE:
<223> OTHER INFORMATION: magnetite binding peptide

<400> SEQUENCE: 16

Tyr Ala Lys Met Lys Ser Arg Asp Ile Glu Ser Ala Gln Ser Asp Glu
1               5                   10                  15

Glu Val Glu Leu Arg Asp Ala Leu Ala
            20                  25
```